US006569672B1

(12) United States Patent
Laugharn, Jr. et al.

(10) Patent No.: US 6,569,672 B1
(45) Date of Patent: *May 27, 2003

(54) PRESSURE CYCLING REACTOR

(75) Inventors: James A. Laugharn, Jr., Winchester, MA (US); Gustav H. Dreier, Jefferson, NY (US); Edwin A. Rudd, Salem, NH (US); David J. Green, Winchester, NH (US)

(73) Assignee: BBI BioSeq, Inc., MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/489,586

(22) Filed: Jan. 21, 2000

Related U.S. Application Data

(63) Continuation of application No. 08/793,213, filed as application No. PCT/US96/03232 on Mar. 7, 1996, now Pat. No. 6,036,923, which is a continuation-in-part of application No. 08/472,304, filed on Jun. 7, 1995, now abandoned, which is a continuation-in-part of application No. 08/399,606, filed on Mar. 7, 1995, now abandoned.

(51) Int. Cl.[7] .............................................. C12M 1/36
(52) U.S. Cl. ................... 435/286.6; 435/288.7; 435/287.2; 422/295; 422/309
(58) Field of Search ......................... 435/286.6, 287.2, 435/288.7; 422/295, 309

(56) References Cited

U.S. PATENT DOCUMENTS

| | | | |
|---|---|---|---|
| 3,750,911 A | 8/1973 | Ebner et al. | 222/254 |
| 3,901,874 A | 8/1975 | Hill et al. | 260/209.5 |
| 4,066,868 A | 1/1978 | Witkin et al. | 219/486 |

(List continued on next page.)

FOREIGN PATENT DOCUMENTS

| | | | |
|---|---|---|---|
| EP | 0602363 A1 | 6/1994 | B01J/3/00 |
| WO | WO 89/03432 | 4/1989 | C12Q/1/68 |
| WO | WO 93/05183 | 3/1993 | C12Q/1/68 |
| WO | WO 93/03135 | 12/1993 | C12N/5/00 |
| WO | WO 94/28745 | 12/1994 | A23L/3/015 |

OTHER PUBLICATIONS

Clegg et al., "Communications to the Editor," Biopolymers, 14:883–887, 1975.
Dreyfus et al., "Effect of Hydrostatic Pressure on the Mitochondrial ATP Synthase," Biochemistry, Am. Chem. Soc., 27:6704–6710, 1988.
Landau, "Hydrostatic Pressure on the Biosynthesis of Macromolecules," [Book], chapter 2, pp. 45–49, [year].
Mozhaev et al., "Exploiting the effects of high hydrostatic pressure in biotechnological applications," Tibtech, 12:493–501, 1994.
Paladini, Jr., et al., "Pressure–Induced Reversible Dissociation of Enolase," Biochemistry, Am. Chem. Soc., 29(9):2587–2593, 1981.
Robert B. Macgregor, Jr. "Reversible Inhibition of EcoRI with Elevated Pressure," Biochemical and Biophysical Research Communications, pp. 775–778 (1990).
Michels et al., "Pressure Dependence of Enzyme Catalysis," Am. Chem. Soc., pp. 108–121 (1992).
K.R. Brower, "A Method for Measuring the Activation Volumes of Fast Reversible Reactions. The Ferric Thiocyanate complex," Journal of American Chemical Society, pp. 5401–5403 (1968).

(List continued on next page.)

*Primary Examiner*—David A. Redding
(74) *Attorney, Agent, or Firm*—Fish & Richardson P.C.

(57) ABSTRACT

Methods and apparatus in which pressure provides precise control over the timing and preferably synchronization of chemical reactions, particularly enzymatic reactions.

27 Claims, 16 Drawing Sheets

U.S. PATENT DOCUMENTS

| | | |
|---|---|---|
| 4,070,008 A | 1/1978 | Schlieckmann .............. 366/159 |
| 4,263,406 A | 4/1981 | Bostick et al. .............. 435/291 |
| 4,297,323 A | 10/1981 | Tetzlaff et al. .............. 422/208 |
| 4,412,552 A | 11/1983 | Kolbanovsky et al. ........ 137/14 |
| 4,636,473 A | 1/1987 | Kleinstreuer ................ 435/298 |
| 4,879,132 A | 11/1989 | Tsuchiya et al. ............ 426/634 |
| 4,987,933 A | 1/1991 | Mack et al. .................... 141/7 |
| 5,027,902 A | 7/1991 | Dickinson et al. .......... 166/369 |
| 5,403,563 A | 4/1995 | Crosbie et al. ............. 422/261 |
| 5,455,175 A | 10/1995 | Wittwer et al. .......... 435/286.1 |
| 5,478,910 A | 12/1995 | Russel et al. ................ 528/274 |
| 5,512,462 A | 4/1996 | Cheng ....................... 435/91.2 |
| 5,658,610 A | 8/1997 | Bergman et al. ............ 426/665 |
| 6,036,923 A * | 3/2000 | Laugharn et al. ........... 422/102 |
| 6,146,884 A * | 11/2000 | Coonrod et al. .............. 34/402 |

OTHER PUBLICATIONS

Miller et al., "High Pressure–Temperature Bioreactor: Assays of Thermostable Hydrogenase with Fiber Optics," Biotechnology and Bioengineering, pp. 1015–1012 (1989).

Michels et al., "Pressure–Enhanced Activity and Stability of a Hyperthermophilic Protease from a Deep–Sea Methanogen", Applied and Environmental Microbiology, vol. 63, No. 10, pp. 3985–3991 (1997).

Kunugi et al., "Effect of Pressure on Plant Endouclease Reactions", Sixteenth Symposium on Nucleic Acids Chemistry, No. 21, pp. 133–134, (1989).

Kunugi, "Use of Pressure for Enzyme Reactions", Tanpakushitsu Kakusan Koso, 34(2), 113–118, (1989).

* cited by examiner

Value Positions

| Steps | 122 | 124 | 152 | 154 | 120b | 178 | 134 | 150b | 170 |
|---|---|---|---|---|---|---|---|---|---|
| 1. | open | closed | closed | closed | retract | | | | |
| 2. | closed | open | open | open | extend drain | | | | |
| 3. | open | closed | closed | closed | retract | | } Pressurize Fluid Path | } Fill Fluid Path | |
| 4. | closed | open | closed | closed | slight extend | | | | |
| 5. | closed | open | closed | closed | limited retraction | vent | | | |
| 6. | closed | open | closed | closed | slight extend | flow | } Pressure Pulse | | |
| 7. | closed | open | closed | closed | slight extend | | | | |
| 8. | closed | open | open | closed | extend | | | | |
| 9. | closed | open | closed | closed | retracts | | | | vent ⎫ |
| 10. | closed | open | closed | open | extend | | | | flow ⎬ More fluid |
| 11. | closed | closed | open | closed | extend | | | | ⎭ |

FIG. 9

PRESSURE CYCLING REACTOR

This is a continuation of application Ser. No. 08/793,213, filed Oct. 28, 1997, now U.S. Pat. No. 6,036,923, which is a national stage application of PCT application Serial No. PCT/US96/03232, filed Mar. 7, 1996, which is a continuation-in-part of U.S. application Ser. No. 08/472,304, filed Jun. 7, 1995, now abandoned, and a continuation-in-part of U.S. application Ser. No. 08/399,606, filed Mar. 7, 1995, now abandoned.

FIELD OF THE INVENTION

The invention is in the general field of apparatus for containing and conducting chemical reactions. The invention also provides methods of using the apparatus to provide control over one or more chemical reactions in a series.

BACKGROUND OF THE INVENTION

Chemical reactions encompass molecular interactions such as the formation and cleavage of covalent bonds and ionic bonds; the association or dissociation of two or more chemical compounds; and changes in primary, secondary, tertiary, or quaternary structure. Chemical reactions include nonenzymatic and enzymatic reactions. Whether or not enzymes are present, a chemical reaction is usually made of several mechanistic steps or molecular interactions, including conformational changes, transition state formation, electron or proton donation/acceptance, and electron rearrangement. Typically, a series of chemical reactions provides a useful chemical product.

For example, in molecular biology, nested sets of deletions are used to create site-directed mutants which are used to probe the function of DNA segments in both structural and regulatory gene sequences. A collection of nested deletions within a gene allows the fine mapping of regions such as enhancers, promoters, and termination sites which are necessary for regulatory functions; and, regions having structural function, such as those defining domains within proteins. It is desirable to create deletions which vary only slightly from each other, for example, by 10–20 base pairs. Existing methods for generating nested sets of deletions digest double stranded DNA with nucleases including restriction endonucleases, Bal31, pancreatic DNase I (DNase I), and Exonuclease III (Exo III).

Restriction endonucleases are used to partially digest a DNA template which contains multiple sites for a given restriction endonuclease. This method requires prior knowledge of restriction sites within a DNA template. Because restriction sites are not randomly distributed throughout a DNA template, many DNA templates will not contain sufficient or properly spaced restriction enzyme sites to generate a useful set of deletion mutants. This is particularly problematic when the mutants are intended to delineate the boundary of regulatory domains.

Turning to another endonuclease, Bal 31 digests double stranded linear DNA from both the 5' and 3' termini. To create a set of unidirectional mutants, a double stranded DNA template (plasmid, phage, or replicative form of M13) is linearized with a restriction enzyme which cleaves at one end of the target sequence. The linearized DNA is incubated with Bal 31. Varying time and the amount of enzyme respectively control the extent of digestion and the rate of digestion. Most commercial preparations of Bal 31 contain two distinct forms of the enzyme, a fast and a slow form, the latter being a proteolytic fragment of the former. The extent of digestion depends on the proportion of the two forms. Each batch of Bal 31 is therefore assayed to determine suitable digestion conditions.

Bal 31 is a processive enzyme which simultaneously degrades both the target DNA and the flanking vector DNA. Bal 31 activity varies with the primary structure of the DNA template; A-T rich,regions are degraded faster than G-C rich regions. Recovery of the truncated target fragments and subcloning into an appropriate vector is required. The processive properties result in the generation of heterogeneous deletions. Bal 31 requires purification because it is inhibited by the presence of RNA.

Turning to a third enzyme, pancreatic DNase I will cut double stranded DNA templates at about the same location on both strands, in the presence of transition metal ions such as $Mn^{2+}$ or $Co^{2+}$. Incubation of closed circular DNA with DNase I generates a set of linear molecules which are cut at locations randomly dispersed throughout the target DNA. A portion of the starting material is never converted to the linear form. After a restriction enzyme cleaves at one end of the target sequence, the sequences are repaired using DNA polymerase, and recircularized. The fraction of clones recovered using this technique can be quite small. DNase I can generate deletions in target DNA contained within, for example, plasmid, phage, or the replicative form of M13 vectors [G. F. Hong, J. Mol. Biol. 158:539 (1982) and Methods Enzymol. 155:93 (1987); S. Labeit et al., Methods Enzymol. 155:166 (1987)].

One method of generating nested sets of deletions is digestion of double stranded DNA with Exo III [L.-H. Guo and R. Wu, Methods Enzymol. 100:60 (1983); S. Henikoff, Gene 23:351 (1984) and Methods Enzymol. 155:156 (1987)]. Exo III degrades double stranded DNA molecules in a 3' to 5' direction from either a 5' overhang or a blunt end. Nested deletions are, generated by digesting the double stranded DNA with two restriction enzymes whose cleavage sites lie, between one end of the target and the binding site for the universal sequencing, primer on the vector. The restriction enzyme cutting nearest to the target DNA must generate either a blunt-end or a 5' overhang. The other enzyme must generate a 3' overhang. As Exo III cannot degrade DNA having a 3' overhang, digestion of the doubly restricted molecule proceeds in a unidirectional manner. Following Exo III digestion for varying lengths of time, the single-stranded regions are removed with a single-strand nuclease such as Mung Bean nuclease. The DNA is then repaired and recircularized. The extent of Exo III digestion is controlled by varying the length of the incubation period. In addition, the temperature may be lowered to decrease the rate of digestion [G. Murphy, in DNA sequencing Protocols, H. G. Griffin and A. M. Griffin, eds., Humana Press (1993) p. 58]. This method requires two restriction enzymes which satisfy the above conditions and which do not cut within the target DNA. This requirement is difficult to satisfy when the target DNA is long.

SUMMARY OF THE INVENTION

The invention features methods and apparatus in which pressure provides precise control over the timing and preferably synchronization of chemical reactions, particularly enzymatic reactions. The disclosed apparatus enables automated and generally rapid changes in pressure. In turn, these pressure changes control chemical reactions, and can control single, pressure-sensitive chemical events, such as the cleavage or addition of a single amino acid or nucleotide. Control and detection of chemical events is particularly useful for synthesizing and characterizing heteropolymers such as nucleic acids and polypeptides.

One aspect of the invention features a pressure cycling reactor which produces programmable fluctuations in the reaction vessel pressure. Preferably the pressure cycling reactor is capable of rapid programmable fluctuations, such as net changes in vessel pressure of about 10,000 to 30,000 psi or more which can be achieved in hundreds of milliseconds or less. The transition time between one pressure and another pressure can be 250 milliseconds, 150 milliseconds, 100 milliseconds, 50 milliseconds, or 30 milliseconds or less.

Pressure is controlled during a sequence of changes. For example, a first pressure $P_1$ is a reaction inhibitory pressure which can be changed to a second pressure $P_2$, a reaction permissive or enabling pressure. The permissive pressure is maintained for a controlled period of time. Then the pressure is changed to a third pressure $P_3$, a reaction inhibitory pressure. Some embodiments permit the addition and removal of reaction mixture components while maintaining the reaction mixture pressure, whether at $P_1$, $P_2$, or $P_3$.

A pressure pulse or pressure cycle is the event including (i) a change from a first to a second pressure, (ii) maintenance of the second pressure for a period of time, and (iii) a change from the second pressure to a third pressure. The first pressure and the third pressure may be substantially different, or may be substantially the same. The second pressure is a pressure sufficient to affect the contents of the reaction vessel in the desired manner, usually enabling a reaction or reaction step to occur.

According to the invention, the pressure cycling reactor includes a reaction vessel for containing a sample, a vessel pressurizer connected to the reaction vessel, and a controller for signalling the pressurizer to maintain reaction inactivating pressure in the reaction vessel and signalling the pressurizer to change pressure in the reaction vessel to a reaction activating pressure for a predetermined short pulsed period and then recycling to a reaction inactivating pressure in the reaction vessel.

In particular embodiments of the invention, the pressurizer changes pressure by over 20,000 psi in less than about 250 milliseconds. The vessel pressurizer includes a pressure chamber, e.g., a pneumatic pump cylinder, connected to the reaction vessel such that the pressure chamber communicates with the reaction vessel responsive to the controller, and a pressure transmitter, e.g., a pneumatic cylinder, connected to a pressure source. The pressure chamber has a variable volume and the position of a pressure chamber wall is controlled by the pressure transmitter to control the volume of the pressure chamber.

A relief valve is used to quickly adjust the pressure in the pressure transmitter thereby creating a pressure pulse in the reaction vessel. A pressure chamber outlet valve is positioned between the pressure chamber and the reaction vessel. A pressure chamber inlet valve is positioned between a fluid source which communicates with the reaction vessel and the pressure chamber. The fluid source includes a fluid reservoir for connection to a reservoir pressure source, and a reservoir control valve, whereby fluids are moved from the fluid reservoir to the reaction vessel via the pressure chamber, while pressure in the reaction vessel is controlled. The temperature of the fluid in the reservoir is controlled by a temperature sensor connected to the fluid reservoir and a reservoir vessel heating and/or cooling source. The temperature of the reaction vessel is controlled by a temperature sensor connected to the reaction vessel and a reaction vessel heating and/or cooling source. The controller monitors the pressure in the reaction vessel with a pressure sensor connected to the reaction vessel. A pressure regulator adjusts the pressure in the pressure chamber and the controller uses feedback from the pressure sensor to control the pressure regulator.

A second vessel pressurizer is connected to the reaction vessel whereby fluids are removed from the reaction vessel while pressure in the reaction vessel is controlled. An inlet valve is located between the reaction vessel and the second vessel pressurizer. An outlet valve is located between the second vessel pressurizer and a second fluid reservoir. A second reservoir control valve is connected to the second fluid reservoir. The controller controls a plurality of valves according to a predetermined set of stored signals which control the valves to add at least one pressurized reagent fluid to the reaction vessel and to remove at least one pressurized reacted fluid from the reaction vessel, while the reaction vessel remains under pressure. A detector, e.g., a radioisotopic detector, an infra-red spectrometer, a mass spectrometer, a gas chromatography-mass spectrometer, a spectrophotometer, a spectrofluorometer, an electrochemical detector, a surface plasmon resonance detector, or a photometer, detects a characteristic of a component present in fluid in or removed from the reaction vessel.

The reaction vessel includes a restraint, e.g., a semi-permeable barrier which divides the reaction vessel into two segments to retain immobilized reagent, e.g., an organic compound attached to a non-liquid support, within the reaction vessel while permitting removal of fluid from the vessel.

According to another aspect of the invention, a reactor for intermittently inhibiting activity of a sample by controlling temperature and pressure conditions of the sample includes a pressurizer in communication with a sample chamber and mounted for movement between a first position for applying a first predetermined pressure to the sample chamber selected to inhibit activity of the sample and a second position for changing the chamber pressure to a second predetermined pressure selected to allow activity of the sample; a switch having a first state and a second state to move the pressurizer between the first position and,the second position; a controller for changing the switch between the first and second states; means for adjusting temperature in the chamber; and a port in communication with the chamber for removal of the sample from the chamber.

According to another aspect of the invention, a reactor for intermittently inhibiting activity of a sample by controlling pressure applied to the sample includes a system for providing flow of test reagent from a fluid reservoir into a sample chamber while the chamber is pressurized. The system includes a first valve located in a first conduit in communication with the fluid reservoir; a second valve located in a second conduit in communication with the sample chamber, a first pressurizer located between the fluid reservoir and the chamber and in communication with the first conduit and the second conduit; and a third valve associated with the first pressurizer for venting the first pressurizer.

With the first valve in an open position and the second valve in a closed position, the reservoir is in communication with the first pressurizer to allow fluid flow to the first pressurizer; with the first valve in a closed position, the second valve in an open position, and the third valve in a closed position, the pressurizer is in communication with the chamber to pressurize the chamber; with the first valve in a closed position, the second valve in an open position, and the third valve cycled between an open position and a closed position, the pressure in the chamber is pulsed.

In particular embodiments of this aspect of the invention, to provide for flow of the test material out of the chamber, the system includes a fourth valve located in a third conduit in communication with the chamber; a fifth valve located in a fourth conduit downstream of the third conduit; a second pressurizer located downstream of the chamber and in communication with the third conduit and the fourth conduit, and a sixth valve associated with the second pressurizer for venting the second pressurizer.

With the first valve in a closed position, the second valve in an open position, the third valve in a closed position, and the fourth valve in a closed position, the pressurizer is in communication with the chamber to pressurize the chamber; with the first valve in a closed position, the second valve in an open position, the third valve cycled between an open position and a closed position, and the fourth valve in a closed position the pressure in the chamber is pulsed; and with the first valve in a closed position, the second valve in an open position, the third valve in a closed position, the fourth valve in an open position, the fifth valve in a closed position, and the sixth valve in an open position the first pressurizer is in communication with the second pressurizer to enable flow through from the first pressurizer through the chamber to the second pressurizer.

One aspect of the invention features a method of controlling an enzymatic reaction step with a rapid pressure cycle or pressure pulse. This method includes providing a sample mixture in a sample vessel at a pressure $P_{i,x}$ at which an enzymatic reaction step is reversibly inhibited (x is an integer $\geq 0$). The sample mixture includes an enzyme. The method also includes the step of changing the pressure of the sample mixture in a length of time $\delta t_{a,y}$ to pressure $P_{a,y}$ at which the enzymatic reaction step can occur (y is an integer $\geq$ to 1). The method also includes the step of changing the pressure of the sample mixture in a length of time $\delta t_{i,z}$ to pressure $P_{i,z}$ at which an additional enzymatic reaction step is reversibly inhibited, where z is an integer greater than or equal to 1, thereby controlling the enzymatic reaction step.

In addition to an enzyme, the sample mixture can include one or more of each of the following in various combinations: a solvent, an enzymatic cofactor, a substrate of the enzyme, an enzymatic inhibitor, a substrate mimetic, and inorganic or organic ions. In most embodiments, the sample mixture includes a substrate. The sample mixture can also include materials on which components of the sample mixture are immobilized for post-enzymatic reaction step 5 retrieval, by which components of the sample mixture are retained within a space of the sample vessel; or by which products or byproducts of an enzymatic reaction are scavenged, adsorbed, associated, or bound by covalent or noncovalent interaction.

One embodiment therefore generates nested deletions wherein the extent of digestion can be finely controlled. Varying amount of enzyme, length of incubation and temperature at atmospheric pressures in addition to pressure results in finer control of the extent of digestion, than methods wherein the pressure is about atmospheric pressure. This embodiment provides groups of deletions having widely or tightly clustered lengths.

The invention features methods of controlling an enzymatic reaction. These methods include providing a sample mixture in a sample vessel at reversibly inactivating pressure, the sample mixture containing an enzyme; exposing the sample mixture to activating pressure; and (iii) exposing the sample mixture to inactivating pressure, thereby controlling an enzymatic reaction. The components of the sample mixture (e.g., one or more substrates of the enzyme, cofactors, transition metal ions, solvent, salts, and buffers) may be provided in any order appropriate to the particular enzymatic reaction or reaction step to be controlled. The enzyme can have distributive or processive properties.

The inactivating pressure is $P_{i,x}$ in step (i), at which pressure an enzymatic reaction step is reversibly inhibited; the activating pressure is $P_{a,y}$ in step (ii) at which pressure the enzymatic reaction step can occur, the exposing step (ii) comprising changing the pressure to $P_{a,y}$ in a length of time $\delta t_{a,y}$; and the inactivating pressure is $P_{i,z}$ in step (iii), at which an additional enzymatic reaction step is reversibly inhibited, the exposing step (iii) comprising changing the pressure to $P_{i,z}$ in a length of time $\delta t_{i,z}$; x being an integer greater than or equal to zero, y being an integer greater than or equal to 1, and z being an integer greater than or equal to 1, thereby controlling the enzymatic reaction.

The method can further include the following steps:
between steps (ii) and step (iii), the activating pressure $P_{a,y}$ is maintained for a time period $t_{a,y}$ corresponding to the average length of a single enzymatic event; or where the substrate is immobilized within the sample vessel, after step (iii) the step of removing a component of the sample mixture from the sample vessel while maintaining the sample vessel pressure, or the step of adding a liquid to the sample mixture while maintaining the sample vessel pressure.

Removed components include a restriction endonuclease, a restriction endonuclease cleavage product, a exonuclease, a nucleotide, or a combination thereof. The removed component can pass through a semi-permeable material when the component is removed from the sample vessel.

The method can further include after step (iii) the step of detecting a characteristic of a component of the sample mixture. Component characteristics include radioactivity, fluorescence, chemiluminescence, molecular ion charge/mass ratio, electrochemical potential, light emission, surface plasmon resonance, and infra-red absorption.

The substrate can be a nucleic acid (e.g., double stranded DNA, single stranded DNA, DNA containing both double and single stranded regions, and RNA, wherein any of the foregoing is immobilized or not immobilized within the sample vessel; and combinations thereof). The enzyme can be a restriction endonuclease, an exonuclease, or a terminal transferase.

The methods can therefore result in at least one cleavage fragment (e.g., nucleotide, amino acid, or oligomer) being cleaved from the nucleic acid substrate.

In one method, there are a first substrate and a second substrate, wherein the enzyme acts to attach the first substrate to the second substrate. In one embodiment, the first substrate is a nucleotide; the second substrate includes an RNA oligonucleotide or a DNA nucleotide; and the enzyme is a polyribonucleotide phosphorylase where the second substrate is an RNA oligonucleotide and a terminal transferase where the second substrate is a DNA nucleotide.

In another embodiment, the first substrate is a nucleotide; the second substrate comprises an RNA or DNA oligonucleotide; and the enzyme is a transferase selected from the enzyme class 2.7.7.

In one embodiment, the substrate is a compound with a chiral or pro-chiral functional group; and the enzyme is a protease, a dehydrogenase, an oxidase, a transferase, a lipase, or an esterase acts on the substrate enantiospecifically.

In another aspect, the enzyme in steps (i)–(iii) is a first enzyme, and the sample mixture in steps (i)–(iii) is a first sample mixture. This aspect further includes after step (iii) the following steps (iv)–(vi): (iv) providing a second sample mixture in a sample vessel, the sample mixture comprising a second enzyme at a reversibly inactivating pressure $P_{i,j}$, the second enzyme being the same as or different from the first enzyme in steps (i)–(iii), and the sample vessel being the same as the sample vessel in steps (i)–(iii) or being a second sample vessel connected to the first sample vessel by a valve; (v) exposing the second sample mixture to a reversibly inactivating pressure; and (vi) exposing the second sample mixture to a reversibly activating pressure, thereby controlling enzymatic reaction steps of the first and second enzymes.

The transition time to pressure $P_{a,k}$ occurs in a time period $\delta t_{a,k}$ to pressure $P_{a,k}$ at which the enzymatic reaction step of the second enzyme can occur. The first and second enzymes can be the same enzyme or different enzymes. The pressure of the second sample mixture is changed in a time period $\delta t_{i,l}$ to pressure $P_{i,l}$ at which an additional enzymatic reaction step of the second enzyme is reversibly inhibited. In some embodiments, reaction inactivating pressure $P_{i,z}$ in step (vi) is substantially the same as $P_{i,l}$.

According to one embodiment, the sample mixture at pressure $P_{i,x}$ is at temperature $T_{i,x}$ whereby the enzyme is inhibited; the sample mixture at pressure $P_{a,y}$ is at temperature $T_{a,y}$, whereby the enzyme is active; and the sample mixture at pressure $P_{i,z}$ is at temperature $T_{i,z}$ whereby the enzyme is inhibited; each of $T_{i,z}$ and $T_{a,y}$ being independently the same as or different from $T_{i,x}$. The values for j, k, and l are the same as x, y, and z, respectively. These subscripts are intended to emphasize that additional steps in pressures may be included, between the described steps (e.g., between step (i) and (ii), there may be a change to a different, not necessarily intermediate, pressure. The method steps can be combined as either repetitive cycles or as nonrepetitive changes in pressure and time, depending on the particular product desired. Moreover, the transition time periods δts are preferably short, e.g., less than 1 second, preferably less than 500, 250, 200, 100 or 50 milliseconds or each of $\delta t_{a,y}$ and $\delta t_{i,z}$ is between 10 and 250 milliseconds or 10 and 50 milliseconds. A pressure may be maintained for a time period, e.g., $t_{a,y}$ or $t_{i,z}$ that range from spike-like transient changes without any measurable plateau to hundreds of milliseconds to seconds (see FIG. 11). For example, the sum $(\delta t_{a,y}+t_{a,y}+\delta t_{i,z})$ is less than or equal to 300, 700, or 1000 milliseconds.

Embodiments also include methods wherein the substrate is immobilized within the sample vessel and the second enzyme is different from the first enzyme, further including between steps (iii) and (iv) the step of removing the first enzyme from the sample vessel while maintaining the sample mixture pressure by eluting with an eluting solution; and methods in which the substrate is a double stranded nucleic acid, the first enzyme is a 5'–3' exonuclease, and the second enzyme is a 3'–5' exonuclease, thereby identifying one or more nucleotides by sequencing with the first enzyme and confirming the one or more nucleotides by sequencing with the second enzyme.

Where steps (i)–(iii) are one cycle, a method can include the steps of repeating the cycle of steps (i)–(iii) at least 49 times, wherein the value for each respective value of $P_{i,x}$, $P_{i,z}$, $\delta t_{a,y}$, $P_{a,y}$, and $\delta t_{i,z}$ in a cycle, is independent of the respective value in any other cycle.

Where steps (iv)–(vi) are one cycle, a method can include the steps of repeating the cycle of steps (iv)–(vi) at least 49 times. A fluid can be added to (or a component removed from) the sample mixture while maintaining the pressure of the sample mixture;

Another aspect is a method of affecting the thermodynamic equilibrium of a reaction, including (i) providing a sample mixture in a sample vessel, the sample mixture being at a pressure $P_0$ and a temperature $T_0$; (ii) changing the sample mixture temperature to $T_1$; (iii) increasing the pressure of the reaction mixture to $P_1$ in a length of time $\delta t_1$, wherein $P_1$ is at least 10,000 psi greater than $P_0$; and (iv) reducing the pressure of the reaction mixture to $P_2$, thereby affecting the thermodynamic equilibrium of the reaction at high pressure.

Embodiments of this aspect include, after the pressure increasing step (iii) the further step of allowing the sample mixture to react; or in which the sample mixture includes a catalyst, after the pressure increasing step (iii) the further step of allowing the product to dissociate from the catalyst; and after step (iii) the further step of removing a component of the sample mixture from the sample vessel.

Another aspect provides a method for treating nucleic acid, including a) providing, in any order: i) a sample vessel, ii) a nucleic acid substrate, iii) an enzyme capable of acting on the nucleic acid substrate, and iv) a pressurizer controlling pressure in the vessel; b) providing the enzyme and tile nucleic acid in solution in the sample vessel and maintaining the enzyme under inactivating pressure conditions; and c) changing the pressure in the sample vessel to an enzyme activating pressure for a controlled period of time, such that the enzyme is active and acts on the nucleic acid substrate for the time period.

The enzyme can be an exonuclease (e.g., Lambda exonuclease), a DNA polymerase or a RNA polymerase; a processive enzyme; a distributive enzyme. The enzyme can modify the nucleic acid substrate, after which a reaction product, such as a cleaved nucleotide, amino acid, or modified substrate, is detected.

The method also includes controlling reaction vessel temperature, wherein the inactivating pressure conditions include a temperature that permits a high level of enzyme activity when reaction vessel pressure is reduced to the enzyme activating pressure. The method can include maintaining the reaction vessel at a low, enzyme inactivating temperature (e.g., less than approximately 5° C.) and an enzyme activating pressure (e.g., approximately 5,000 to 15,000 pounds per square inch), raising the pressure to an enzyme inactivating pressure, lowering the temperature to an enzyme activating temperature (e.g., an integral temperature between 15° C. to 20° C.), and then lowering the pressure to an enzyme activating pressure.

For example, the method includes a) maintaining the enzyme at an inactivating temperature of less than approximately 5° C., thereby rendering the enzyme substantially inactive; b) adding the nucleic acid substrate to the inactive enzyme to create a reaction mixture; c) increasing the pressure in the sample vessel to an enzyme inactivating pressure of greater than approximately 30,000 pounds per square inch; d) raising the temperature of the reaction mixture in the sample vessel to greater than approximately 10° C.; and e) for a controlled period of time, lowering the pressure in the sample vessel to an enzyme activating pressure of less than approximately 20,000 pounds per square inch, thereby rendering the enzyme active such that the enzyme acts on the nucleic acid substrate. The method can include f) raising the pressure in the sample vessel to an enzyme inactivating pressure.

The method can also include the further steps of steps of changing the pressure in the sample vessel to an enzyme inactivating pressure; and repeating a cycle of steps c) and d) at least once, at least five times. The enzyme inactivating pressure is generally higher than the enzyme activating pressure.

Other features and advantages of the invention will be apparent from the following description of the drawings, the detailed description, examples, and from the claims.

BRIEF DESCRIPTION OF THE DRAWINGS

FIG. 9 is a listing of valve positions during steps of the fluid control algorithm.

DEFINITIONS

Figure 1:
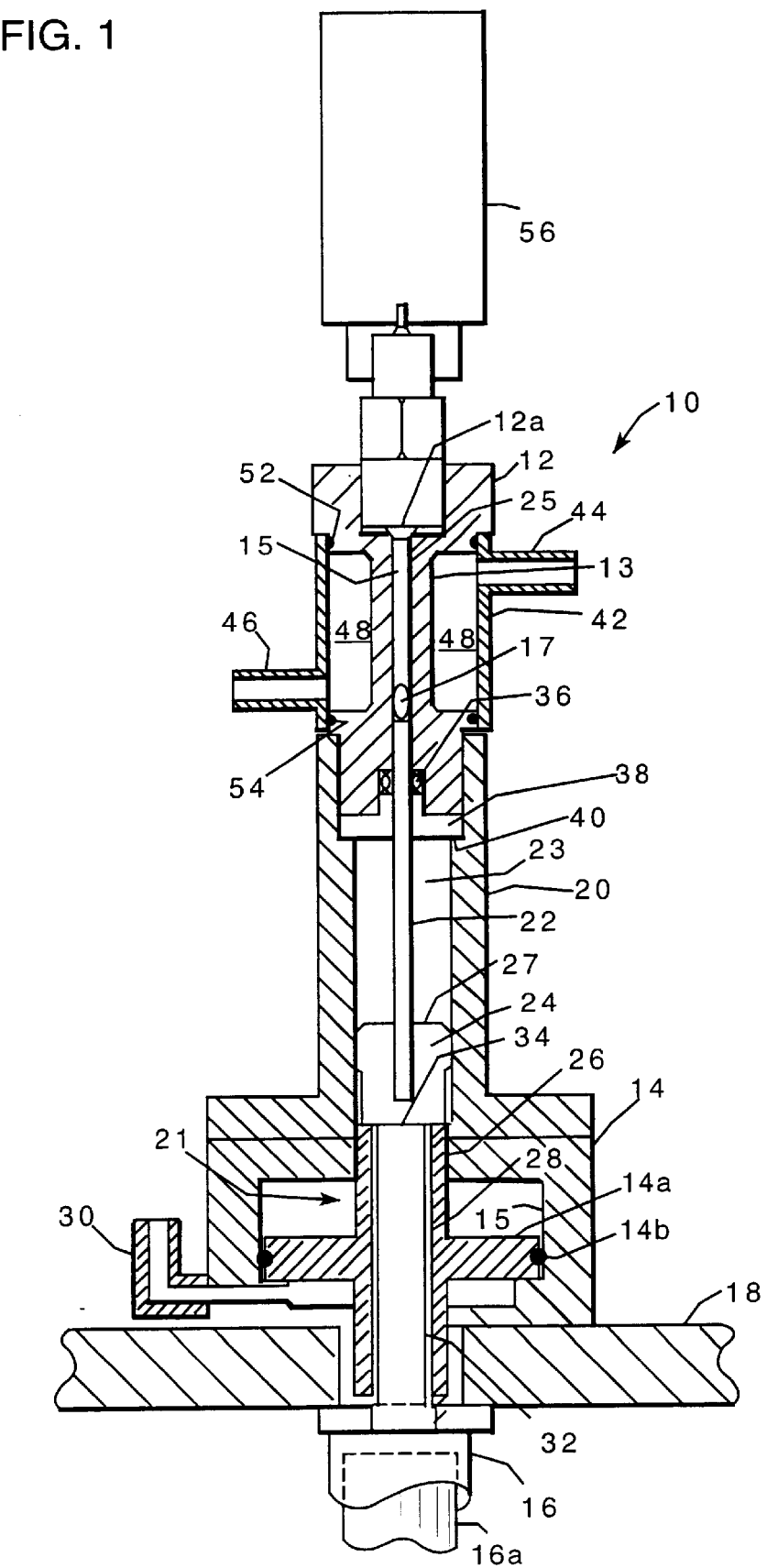
FIG. 1 is a, schematic of a reactor according to the invention.

To facilitate understanding of the invention, a number of terms are defined below and elsewhere in the disclosure.

A sample mixture is a fluid. A fluid can be a liquid or a gas. Liquids include aqueous and organic solutions. Depending on the application, the sample mixture may or may not include an enzyme at a given step.

Aqueous sample mixtures include components such as (a) water (e.g., tap, distilled, filtered, deionized, degassed, or deuterated), and (b) at least one of (i) inorganic cations and anions, (ii) organic compounds, and (iii) solvated gases. Sample mixtures are generally solutions, referring to a fluid (solvent) having a solute that is dissolved, or suspended (undissolved). Sample mixtures can also include enzymes or enzyme substrates which are immobilized on polymer, ceramic, or composite beads or surfaces. These immobilized sample mixture components are not necessarily dissolved or suspended in the sample mixture, but can be exposed to sample mixture components and mixed by fluid turbulence.

Inorganic cations include lithium, sodium, potassium, magnesium, calcium, chromium, iron, manganese, zinc, cobalt, copper, and aluminum. Inorganic anions include fluoride, chloride, bromide, iodide, sulfate, phosphate, hydrogen phosphate, carbonate, and bicarbonate.

Organic compounds include natural and synthetic nucleic acids, nucleotides, oligonucleotides, α-amino acids, oligopeptides, peptidomimetics, depsi-peptides, peptides, saccharides, liposaccharides, and mixtures thereof. Nucleotides include deoxynucleoside 5'triphosphates such as dATP, dCTP, dCTP, dTTP, and dUTP; dideoxynucleotides; nucleotides for resolving sequencing ambiguities such as $c^7dGTP$, dITP, and $c^7dATP$; 2'-deoxynucleoside-5'-O-(1-thiotriphosphates) such as dATPαS; 5-methyldeoxycytidine 5'-triphosphate; ribonucleoside 5'-triphosphates; 2'3'-ddNTPs; and 7-deaza 2'-dNTPs.

Examples of amino acids include the twenty common α-amino acids (Gly, Ala, Val, Leu, Ile, Ser, Thr, Asp, Asn, Lys, Glu, Gln, Arg, His, Phe, Cys, Trp, Tyr, Met, and Pro); and other natural or synthetic amino acids (e.g., norleucine, ethylglycine, ornithine, methylbutenylmethyl-threonine, phenylglycine, γ-carboxyglutaric acid, β-hydroxyproline, γ-hydroxyproline, δ-hydroxylysine, methylated amino acids, and ε-iodo, ε1-ε2-diiodo, ε-nitro-, ε-amino- and O-acetyl-tyrosine).

Saccharides include glucose, fructose, galactose, mannose, sucrose, and other naturally-occurring substituted saccharides. Organic compounds also include radiolabelled compounds, and other compounds with detectable tags or signals.

Organic sample mixtures include components such as
  (a) an organic solvent or mixture thereof (e.g., methylene chloride, tetrahydrofuran, dimethyl formamide, ether, benzene, toluene, hexane, and ethyl acetate), and
  (b) a organic reagent.

Turning to the other type of fluid, gases include the noble gases (e.g., He, Ne, and Ar); gases used as reagents in organic synthesis such as HCl, HF, diatomic hydrogen, and diatomic halogens; and atmospheric gases used as reagents in biological systems such as carbon dioxide, carbon monoxide, and oxygen. Exposing the reaction chamber to a pressurized gaseous fluid can: (a) increase or decrease the pressure of the reaction vessel, (b) change the pH, (c) provide a reagent for a chemical or enzymatic reaction, whether the gaseous fluid reagent partially dissolves in liquid, if any, that is present in the reaction chamber or is present in the gaseous phase, if any, in the reaction vessel, (d) quench a chemical or enzymatic reaction step, and (e) move fluid contents into or out of the reaction vessel.

A vector (or vehicle) is a nucleic acid molecule that transfers a DNA segment or segments from one cell to another. An expression vector is a recombinant DNA molecule containing a desired coding sequence and nucleic acid sequences necessary for the expression of the operably linked coding sequence in a particular host organism. Nucleic acid sequences necessary for expression in procaryotes usually include a promoter, an operator (optional), and a ribosome binding site. Eukaryotic cells are known to utilize promoters, enhancers, and termination and polyadenylation signals.

Complementarity may be partial, wherein only some of the bases are matched according to the base pairing rules, or complete. The degree of complementarity between nucleic acid strands significantly affects the efficiency and strength of hybridization between nucleic acid strands. Complementarity therefore bears on the accuracy of amplification reactions, as well as detection methods dependent upon binding between nucleic acids.

Hybridization is the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. $T_m$ is the melting temperature, or the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (see e.g., Anderson and: Young, Quantitative Filter Hybridization, in *Nucleic Acid Hybridization* (1985). Other references include more sophisticated calculations which take structural as well as sequence characteristics into account for the calculation of $T_m$.

Stringency refers to the conditions of temperature, ionic strength, and the presence of other compounds such as organic solvents, under which nucleic acid hybridizations are conducted. Under high stringency conditions, nucleic acid base pairing will occur only between nucleic acid fragments that have a high frequency of complementary base sequences. Under weak or low stringency conditions, nucleic acids that are derived from organisms that are genetically diverse will occur, even though the frequency of complementary sequences is usually less.

"Nucleic acid" and "nucleic acid substrate" encompass DNA, RNA, and PNA (peptide nucleic acids), whether single stranded, double stranded, or a single strand with intermittent complementary segments, or a combination thereof. Chimeric oligonucleotides having stretches of both RNA and DNA residues on the same, oligonucleotide are commercially available from, for example, Oligos Etc., Inc (Wilsonville, Oreg.). The present invention does not, in principle, limit the length of the nucleic acid; the nucleic acid may be genomic or a defined length (e.g. short oligonucleotides) or fragments thereof (including single bases). A nucleic acid may be obtained from any source and therefore may be naturally occurring; naturally occurring and purified; or produced synthetically, recombinantly or by amplification. Nucleic acids include modified nucleic acids formed by an enzyme which removes a nucleotide from the nucleic acid substrate, or adds a chemical moiety, such as a terminal methyl group, or a linking group to bond the nucleic acid to another molecule. As discussed elsewhere, a nucleic acid may be immobilized on a polymer or composite bead, matrix, or other support surface.

Nucleic acids which may be amplified by any amplification method. An amplifiable nucleic acid will usually include a sample template, i.e., a nucleic acid originating from a sample. In contrast, a background template may or may not be present in a sample, and is generally an inadvertent result of carryover, or the presence of nucleic acid contaminants sought to be purified away from the sample. For example, nucleic acids from organisms other than those to be detected may be present as background in a test sample. An example of an amplification method is a polymerase chain reaction (PCR), such as the method of K. B. Mullis U.S. Pat. Nos. 4,683,195 and 4,683,202, hereby incorporated by reference, which describe a method for increasing the concentration of a segment of a target sequence in a mixture of genomic DNA without cloning or purification.

"Sample" is used in its broadest sense. A sample includes a specimen, culture, biological sample, environmental sample, etc. from human and animal samples as well as naturally occurring and synthetic material. The term "sample vessel" is used to indicate a means for containing a sample, whether by enclosing a sample (e.g., in a batch format) or by using a sample in an enclosed device (e.g., channeling both within and between a chamber, channel or stream). Similarly, a "reaction vessel" is not limited to any one design; typically it is a sample vessel in which a reaction takes place.

A reaction or sample mixture refers to a combination of two or more components. Optimum enzymatic temperature is the temperature at which an enzyme is most active, under a given pressure, and solvent system (solvents and salts). The optimum varies with each enzyme, but is generally in the range 10–80° C., and more particularly between 25–37° C. Optimal temperatures can be found in product literature provided, for example, by New England BioLabs (NEB).

A substantially inactive enzyme exhibits less than 20%, and generally less than 10%, of its activity at optimum enzymatic temperature (**and atmospheric pressure?) (100% activity). Ideally, an inhibited or substantially inactive enzyme is completely inactive (0% activity), but determination of this is limited by the sensitivity and uncertainty of a given activity assay. A reversibly inhibited enzyme exhibits no activity under restrictive or inhibitory conditions, and yet resumes activity when exposed to permissive conditions. A pause or transition period can occur after permissive conditions are imposed, but before enzymatic activity resumes. Permissive conditions include those conditions under which optimum enzymatic activity occurs, and also those conditions under which slower, but measurably useful activity occurs.

A primer is an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

A probe is an oligonucleotide, occurring naturally as in a purified restriction digest or produced synthetically, which is capable of hybridizing to another oligonucleotide of interest. Probes are useful in the detection, identification and isolation of particular gene sequences. A probe, the particular gene sequence, or both can be labelled with any "reporter molecule," so that the probe, the particular gene sequence, or both are detectable in enzyme (e.g., ELISA, as well as enzyme-based histochemical assays), fluorescent, radioactive, and luminescent detection systems.

A target sequence is the region of nucleic acid bounded by the primers used for detection and/or amplification (e.g., by the polymerase chain reaction). Thus, it is desirable to identify the target from among other sequences. A segment is a region of nucleic acid within the target sequence.

A PCR product or amplification product is the resultant mixture of compounds after two or more cycles of the steps of denaturation, annealing, and extension. These terms encompass the case where there has been amplification of one or more segments of one or more target sequences.

Amplification reagents are those reagents needed for amplification exclusive of primers, a nucleic acid template, and an amplification enzyme. Amplification reagents include deoxyribonucleoside triphosphates and buffer. Typically, amplification reagents and other reaction components are placed in a reaction (e.g., sample) vessel (test tube, microwell, pressure deformable casing with optional outlets, etc.).

Restriction endonucleases and restriction enzymes refer to enzymes (e.g., bacterial enzymes), each of which cuts double-stranded DNA at or near a specific nucleotide sequence.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the term "an oligonucleotide having a nucleotide sequence encoding a gene" means a DNA sequence comprising the coding region of a gene or in other words the DNA sequence which encodes a gene product. The coding region may be present in either a cDNA or genomic DNA form. Suitable control elements such as enhancers/promoters, splice junctions, polyadenylation signals, etc., may be placed in close proximity to the 0oding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc., or a combination of both endogenous and exogenous control elements.

Enzymes that synthesize or digest polymer substrates may dissociate from the substrate after each catalytic event, i.e., they may be nonprocessive (coextensive with distributive). On the other hand, they may remain bound to the polymer until many cycles of reaction are completed, i.e., they may be "processive." Regarding enzymes, the terms processive, non-processive, and distributive are used in the art (see, e.g., A. Kornberg and T. A. Baker, *DNA Replication*, 2nd ed. (Freeman and Co. 1992.)).

DETAILED DESCRIPTION OF THE INVENTION

A. Introduction

The invention features a pressure cycling reactor which produces rapid programmable fluctuations in the pressure of a reaction vessel. The pressure fluctuations can be programmed with many profiles. Where a fluctuation between two pressures P and P' occurs, for example, various profiles include a) wherein the length of time at each of P and P' is about the same; b) wherein the length of time at P is greater than the length of time at P'; c) wherein the transition time from P to P' is about the same as the transition time from P' to P; d) wherein the transition time from P to P' is longer than the transition time from P' to P; and e) wherein there are several pauses at intermediate pressures in the transition from P to P', but the jump from P' to P is very rapid. Furthermore, pressure fluctuation profiles may include more than two pressures P and P', such as fluctuating in small steps or large jumps between different pressures with little repetition.

The invention also provides a pressure cycling reactor capable of adding and removing components within the reaction vessel while maintaining or even increasing the pressure of the reaction vessel. Components can be added or removed in many permutations with a pressure fluctuation profile; each pressure pulse cycle need not be identical.

The pressure cycling reactor is therefore useful in applications wherein at least one step of a reaction, is pressure-sensitive. These reactions include enzymatic, nonenzymatic, chemical, physical, kinetic, and thermodynamic reactions; in other words, pressure-sensitive interactions include covalent (bond breaking and bond formation), noncovalent, ionic (solvation), and van der Waals forces; hydrophobic or hydrophilic interactions; and structural conformations (secondary, tertiary, and quaternary, i.e., folding, and formation of helices and sheets).

The rate of a reversibly pressure-sensitive reaction step can be decreased, stopped, increased, or started, the latter being achieved when a reversibly inhibitory pressure is rapidly changed to a permissive pressure. In general, the rates of multiple enzymes (same or different enzyme) can be synchronized by reversibly inhibiting them at an inhibitory pressure (e.g., a high pressure), and then rapidly changing the pressure to a permissive pressure.

The pressure reactor can contain multiple sample vessels, in parallel or in series, to perform combinatorial or sequential operations, respectively, wherein at least one reaction step is pressure-sensitive. Multiple sample vessels (or even the larger reaction vessels) can be interconnected, so portions of reacted sample mixtures can be transferred from one sample vessel to another sample vessel to undergo a subsequent treatment. Combinatorial synthesis of oligonucleotides (including preparation of constructs), peptides, and other organic compounds can be performed in this manner.

B. Pressure Cycling Reactor

Referring to FIG. 1, a reactor 10 includes a reaction module 12 having a wall 13 defining a chamber 15 for containing a sample capsule 17, made from, e.g., polyethylene. A port 12a in reaction module 12 permits placement of capsule 17 into chamber 15. A short stroke pressure transmitting pneumatic cylinder 14 and a pressure transmitting hydraulic cylinder 16 for applying pressure to chamber 15 are mounted to a base plate 18. Reaction module 12 is supported by a truss 20 made of, e.g., stainless steel, defining a variable volume pressure chamber 23. A piston 22 having, e.g., a 3/16" diameter, supported and guided by a bearing 24 made from, e.g., a bronze alloy, and defining a chamber wall 27 communicates between a bore 25 in reaction chamber 12 and cylinders 14 and 16. Piston 22 along with cylinders 14 and 16 form a vessel pressurizer 21 which controls the pressure in chamber 15. Reaction module 12 is made from, e.g., stainless steel and bore 25 has a diameter of about 0.188" and a length of about 1".

Figure 1A:
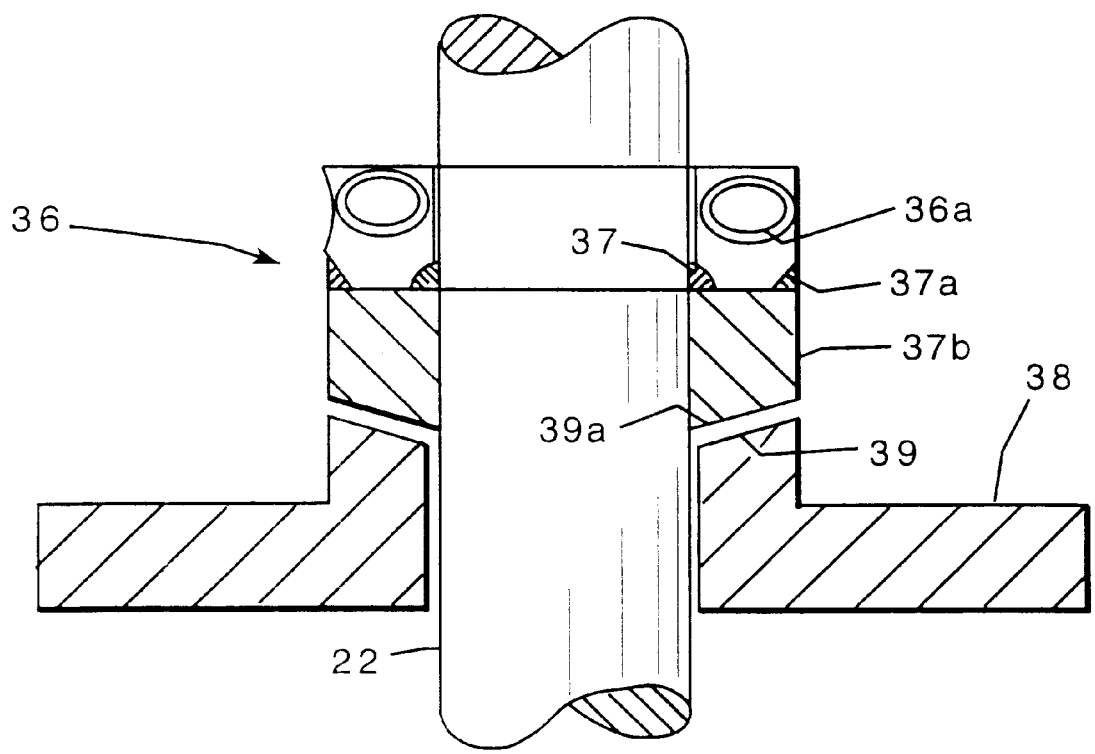
FIG. 1A shows a spring seal and gland washer of the reactor of FIG. 1.

Referring also to FIG. 1A, a seal 36, e.g., a spring energized seal including a spring 36a and back-up washers 37, 37a, and 37b available from Bal Seal Engineering Co. Inc., Santa Ana, Calif., supported by, e.g., a gland washer 38, seals piston 22 within reaction chamber 12. Gland washer 38 includes an inclined surface 39 which mates with an inclined surface 39a of back-up washer 37b. Spring 36a ensures sealing at low pressures and assists sealing at higher pressures. The back-up washers and the gland washer act to prevent extrusion of seal 36 under pressure. Gland washer 38 is supported by a shelf 40 in truss 20.

Pneumatic cylinder 14 includes a piston 14a having, e.g., a 2.5" diameter, with an extension rod 26 having a through bore 28. O-ring 14b forms a seal between piston 14a and an inner wall 15 of pneumatic cylinder 14. When pneumatic cylinder 14 is energized, pressure on piston 14a is transmitted to guide bearing 24 by rod 26 creating an upward force on piston 22. This force is adjustable by varying the pressure to the pneumatic cylinder from a source (not shown) attached to inlet 30. The force applied to piston 22 by pneumatic cylinder 14 determines the low pressure level within reaction chamber 12 during pressure pulsing. Pneumatic cylinder pressure is adjustable up to about 100 psi (which produces a pressure of about 17,000 psi in reaction chamber 12).

Hydraulic cylinder 16 includes a piston 16a having, e.g., a 1" diameter, with an extension rod 32 projecting up through bore 28 of pneumatic cylinder rod 26. The end 34 of hydraulic rod 32 bears against guide bearing 24. On extensions hydraulic rod 32 drives piston 22 upwards. The pressure generated by hydraulic cylinder 16 plus the pressure generated by pneumatic cylinder 14 determines the high pressure level in the reaction chamber. Hydraulic cylinder pressure is adjustable with an upper limit set at approximately 1,500 psi. The ratio of the cross-sectional area of hydraulic piston 16a to the cross-sectional area of piston 22 is 28.4:1.

Reaction module 12 is surrounded by a thermostatting jacket 42 to control the temperature of the reaction chamber. Jacket 42 has inlet and outlet fittings 44, 46, respectively, which permit fluid to be circulated into chamber 48 surrounding wall 13 from a temperature controlled heating/refrigeration bath (not shown). Around the top and bottom of reaction chamber 12 are O-rings 52, 54 which provide a fluid seal for thermostatting jacket 42. A thermocouple (not shown) is mounted to reaction chamber 12 to monitor the temperature of the chamber. The temperature of chamber 12 is controlled within a range of about −15° C. to +40° C. with an accuracy of about +/−1° C. The thickness, e.g., 3/16", of wall 13 is selected to be thin enough to permit heat transfer from thermostatting chamber 48 to sample chamber 15 while being thick enough to withstand the pressures applied to sample chamber 15. The maximum allowable pressure in reaction module 12 as determined by the thickness of wall 13 as well as by the performance of seal 36 is about 40,000 psi.

Mounted at the top of the assembly is a pressure transducer 56, for example, a 75,000 psi, +/−0.5% accuracy strain gauge type transducer available as part number HP/5651-02-02 from Sensotec, Inc., Columbus, Ohio. Pressure transducer 56 is removed from reaction module 12 to allow access to port 12a.

Figure 2:
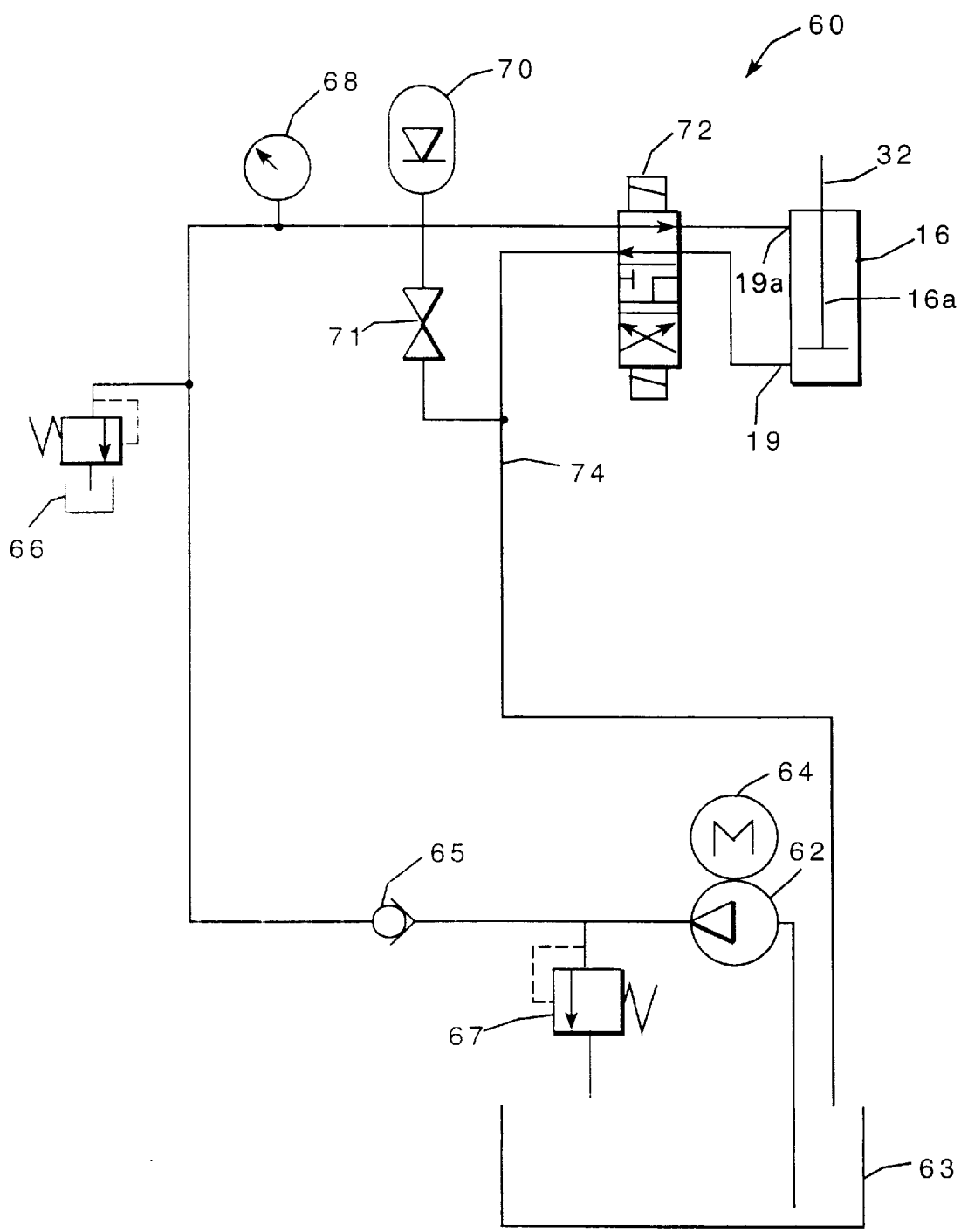
FIG. 2 is a schematic of the hydraulic system of the reactor of FIG. 1.

Referring to FIG. 2, hydraulic pressure is delivered to hydraulic cylinder 16 by an hydraulic pump 62. An hydraulic system 60 includes hydraulic pump 62 driven by a motor 64, a fluid reservoir 63, a relief valve 67, a check valve 65, a pressure adjustment valve 66, a pressure gauge 68, an accumulator 70, a manual valve 71, a four-way directional control valve 72, and hydraulic cylinder 16.

Motor 64 is, e.g., a 2 HP electric motor with an output of 0.8 GPM at 3,000 psi max. Actual system pressure is controlled by pressure adjustment valve 66 and is variable up to the set upper limit of approximately 1,500 psi.

Directional control valve 72 is, e.g., a three position spring centered spool valve actuated by dual electrical solenoids, available as Bosch part #9810231072 from Pearse-Pearson, Inc., Milford, Mass. With both solenoids de-energized, both hydraulic cylinder ports 19, 19a are connected to a drain line 74, and cylinder piston 16a may be freely moved. In use, energizing one solenoid pressurizes port 19 and with the other solenoid deenergized so that it is open to drain line 74, piston 16a is forced to extend thus pressurizing sample chamber 15. To now pulse the pressure in the sample chamber, both solenoids are deenergized so piston 16a is free to move and the pressure in chamber 15 forces piston 22 down releasing the pressure in the chamber (to the level of pressure applied by pneumatic cylinder 14). Alternatively, energizing the other solenoid pressurizes port 19a and with the other solenoid deenergized so that it is open to drain line 74, piston 16a is forced to retract. The passive release of pressure from chamber 15 is preferable because it provides for a faster hydraulic response time and the continual contact between piston 22 and rod 32 avoids producing impact loads between the piston and the rod. Directional control valve 72 can be rapidly switched at times down to 20–25 ms to apply pressure to hydraulic cylinder 16 and to allow release of pressure from chamber 15.

Hydraulic accumulator 70 is mounted near directional control valve 72 to enhance response and dampen pressure fluctuations. Accumulator 70 has, e.g., a one quart capacity and is charged by pump 62 to hydraulic system line pressure. The presence of check valve 65 causes accumulator 70 to remain charged after pump 62 is turned off. Manual valve 71 is used to discharge the accumulator and depressurize the hydraulic system. Relief valve 67 limits the maximum delivered pressure from pump 62.

Figure 3:
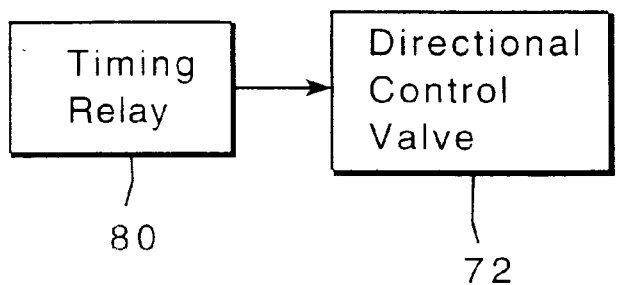
FIG. 3 is a block diagram of the control of the reactor of FIG. 1.

Referring to FIG. 3, reactor 10 is controlled by a timing relay 80 having an adjustable pulse width and duty cycle. Outputs from timing relay 80 control directional control valve 72. Pressure sensor data can be monitored with a computer or oscilloscope. The reaction chamber pressure applied by pneumatic cylinder 14 and hydraulic cylinder 16 is adjustable with an accuracy of about +/−200 psi. The dwell at the low pressure after the pressure is pulsed from high pressure and before pulsing back to high pressure is adjustable from about 30 msec to several minutes. The timing accuracy is about +/−10 msec.

In use, e.g., with an enzyme, capsule 17 containing about 50 ul of sample held at an inhibiting temperature, e.g., by freezing the sample in the capsule, is placed in chamber 15. Chamber 15 is then filled with, e.g., silicon oil, to enable the applied pressure to be transferred to the capsule. Alternatively, to control the onset of enzyme reaction, a reaction capsule can include a barrier which segregates the DNA and enzyme until pressure is applied. Pressure transducer 56 is then attached to reaction module 12. The first application of pressure to chamber 15 ruptures the capsule barrier, causing the DNA and enzyme to combine.

Pneumatic cylinder 14 controls the pressure in chamber 12 when hydraulic cylinder 16 is not pressurizing the chamber, i.e., when the enzyme is not inhibited. Since enzyme processing begins to slow under pressures of between 10,000 and 20,000 psi, it may be desirable to slow the reaction to optimize single base stepping during DNA sequencing, pneumatic cylinder 14 acts to limit the magnitude of the pressure drop during pulsing. Thus, both the level of inhibiting pressure (applied by pneumatic cylinder 14 and hydraulic cylinder 16) and the activation pressure (applied by pneumatic cylinder 14) can be individually controlled.

Figure 4:
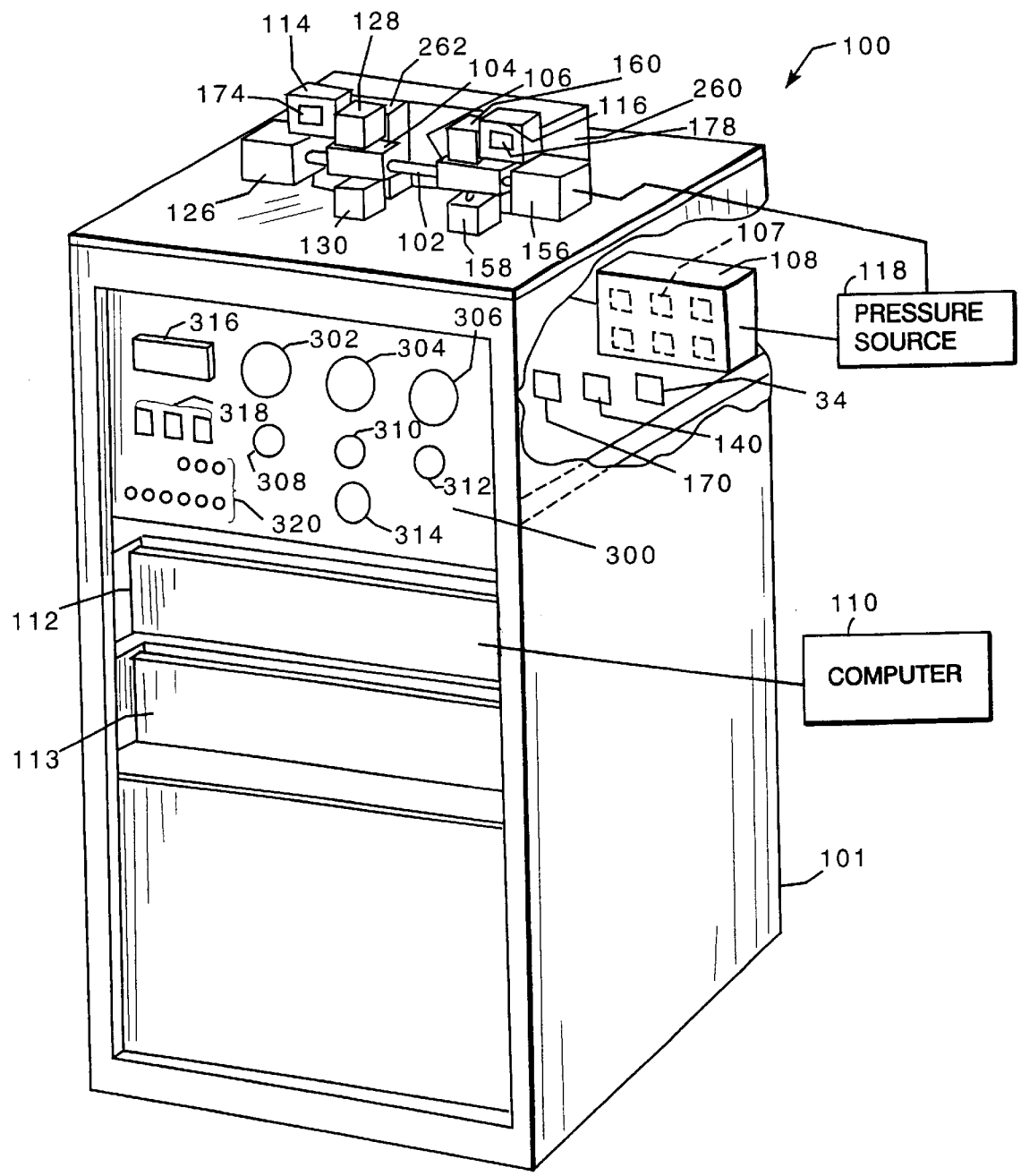
FIG. 4 is an illustration of an alternative embodiment of a reactor.

Referring to FIG. 4, in a preferred, alternative embodiment, a computer controlled, flow through pressure cycling reactor 100 is an electro-pneumatically operated fluid handling apparatus which is capable of reacting samples of selected materials in a pressure modulated flow environment. Utilizing an arrangement of fluid pumps and valves, a sample may be exposed to a variety of reagents while at the same time being maintained in a steady or rapidly changing pressure environment. Fluid pressure is adjustable up to a level of about 40,000 psi, and the fluid pressure can be rapidly reduced to a significantly lower level and then back to the higher level in a matter of milliseconds. While a pnuematic system is described, it is understood that other systems, e.g., an hydraulic system can be employed.

Pressure cycling reactor 100 includes a cabinet 101 on which are mounted a reaction vessel 102, a first vessel pressurizer, injection pump/valve module 104, and a second vessel pressurizer, drain pump/valve module 106. It is understood that the roles of modules 104 and 106 can be reversed. A series of pneumatic valves 107 in a pneumatic valve module 108 direct and switch pressurized gas to pressure transmitting pneumatic cylinders 126, 128, 130, 156, 158, and 160 mounted on cabinet 101, which control the fluid pumps and valves in modules 104, 106, discussed further below. Fluid reservoirs 114, 116 mounted on cabinet 101 supply reagents to pump/valve modules 104, 106, respectively.

A pressure source 118, e.g., an air compressor or compressed gas bottle, pressurizes fluid reservoirs 114, 116 and also supplies pressure to pneumatic valves 107. The fluid reservoirs are pressurized, e.g., to approximately 10 psi, to facilitate flow and prevent formation of a vacuum in the flow path. The valve module, pneumatic valves, and fluid reservoirs are mounted to a clamp 260, discussed further below.

A computer 110 times and controls the pressure pulsing and fluid flow, and monitors the system status. Two signal conditioning units 112, 113 provide input and output signal amplification and scaling.

Display panel 300 includes pressure gauges 302, 304, 306 which monitor the pressure applied to fluid reservoirs 114, 116 and pneumatic valves 107. Knobs 308, 310, 312 adjust a series of pressure regulators 180, 182, 184 (see FIG. 5A), which control the pressure applied to fluid reservoirs 114, 116 and pneumatic valves 107. Knob 314 adjusts a main shut off valve 118c (see FIG. 5A). A digital display 316 indicates the pressure within reaction vessel 102 as read by a pressure transducer 188 (see FIG. 5). Power switches 318, e.g., illuminated rocker switches, are the master power switch, the data acquisition power switch, and the pneumatic valve power switch. Indicator lights 320 indicate the states of the pneumatic valves and also serve as manual override push button switches.

Figure 5:
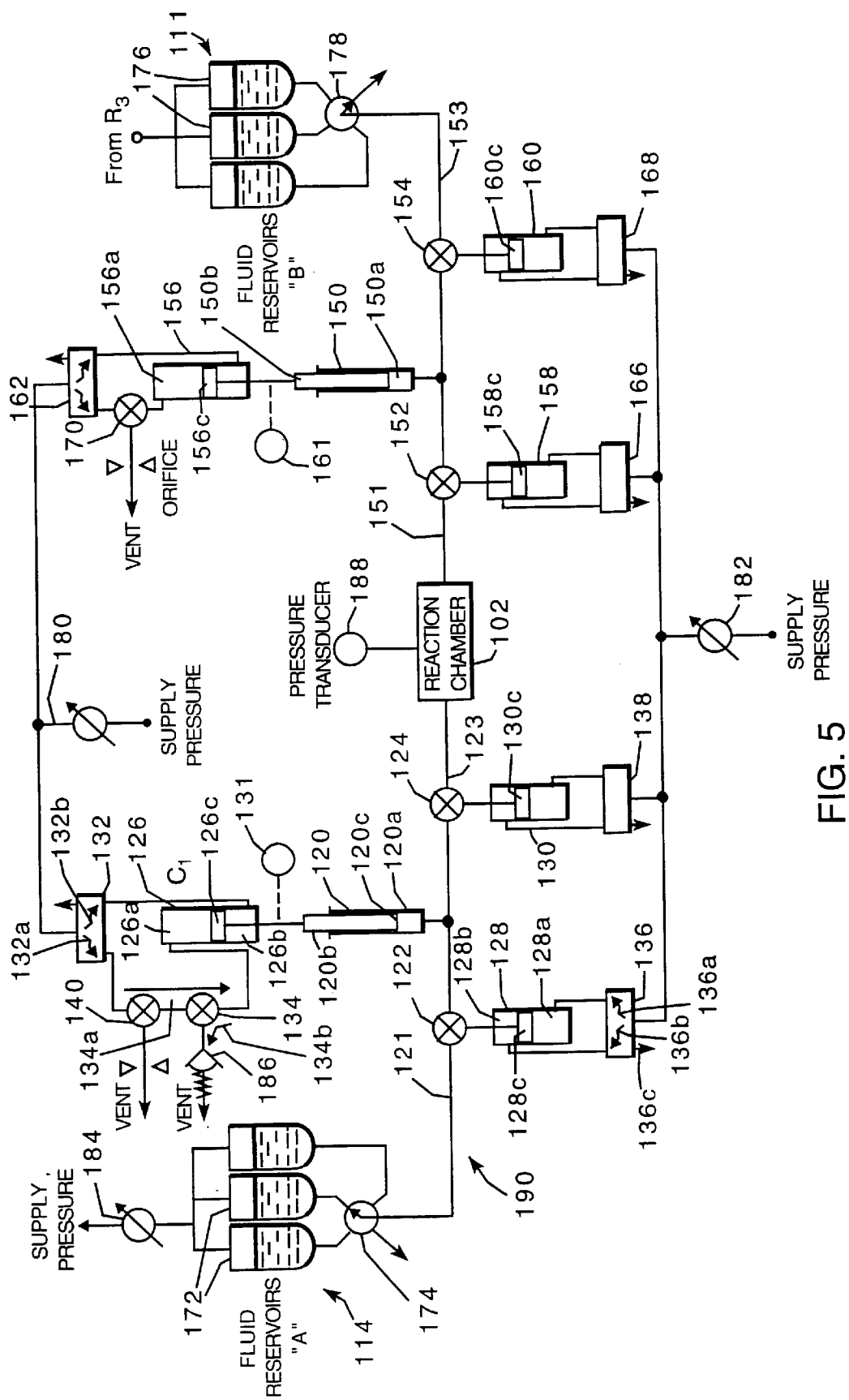
FIG. 5 is a schematic of the components of the reactor of FIG. 4.

Referring to FIG. 5, injection pump/valve module 104 (see FIG. 4) includes a piston type injection pump 120 for generating hydraulic pressure to move fluid along a flow path 190, and high pressure on-off injection pump inlet and outlet valves 122, 124 respectively for controlling movement of fluids and for sealing pressure within flow path 190.

Inlet valve 122 is located within a conduit 121 running from a valve 174 (described below) to injection pump 120, and outlet valve 124 is located within a conduit 123 running from injection pump 120 to reaction vessel 102. Pump 120 communicates with conduits 121 and 123. Pneumatic cylinder 126 provides the mechanical force to drive pump 120, pneumatic cylinder 128 operates pump inlet valve 122, and pneumatic cylinder 130 operates pump outlet valve 124. A position sensor 131 provides a signal when injection pump 120 is just short of bottoming out, i.e., a piston 120b of pump 120 is near full extension.

Four-way pneumatic valves 132, 136, and 138 located in pneumatic valve module 108 control the flow of gas from pressure source 118 to and from cylinders 126, 128, and 130, respectively, to control the motion of cylinder rods 126c, 128c, and 130c respectively.

Referring, for example, to valve 136, a first flow path (arrow 136a) pressurizes a first chamber 128a of cylinder 128 to close valve 122, a second flow path (arrow 136b) pressurizes a second chamber 128b of cylinder 128 to open valve 122, and an exhaust port 136c vents to atmosphere.

A three-way pneumatic relief valve 134 located in cabinet 101 enables rapid pressure release and recharging of a first chamber 126a of cylinder 126 in order to generate a positive or negative pressure pulse. A three-way pneumatic valve 140 located in cabinet 101 allows slow venting of pressure from chamber 126a. A first flow path 132a through valve 132, with valves 134 and 140 in position to allow gas flow along arrow 134a, pressurizes first chamber 126a of cylinder 126 to extend piston 120b of pump 120, and a second flow path 132b pressurizes a second chamber 126b of cylinder 126 to retract piston 120b. Piston 120b defines a pressure chamber wall 120c which controls the volume of pressure chamber cylinder 120a.

Similarly, drain pump/valve module 106 includes a piston type drain pump 150, and high pressure on-off drain pump inlet and outlet valves 152, 154. Inlet valve 152 is located within a conduit 151 running from reaction vessel 102 to drain pump 150, and outlet valve 154 is located within a conduit 153 running from drain pump 150 to a valve 178 (described below). Pump 150 communicates with conduits 151 and 153. Pneumatic cylinder 156 provides the mechanical force to drive pump 150, pneumatic cylinder 158 operates pump inlet valve 152, and pneumatic cylinder 160 operates pump outlet valve 154. A position sensor 161 provides a signal when drain pump 150 is just short of bottoming out, i.e., near minimum volume. Fluid volumes and flow rates are controlled by pumps 120 and 150. A piston 150b of pump 150 defines a pressure chamber wall 15c which controls the volume of a variable volume pressure chamber pump cylinder 150a. The maximum volume of cylinder 150a is substantially greater than the volume of fluid in reaction vessel 102.

Four-way pneumatic valves 162, 166, and 168 located in pneumatic valve module 108 control the flow of gas from pressure source 118 to and from cylinders 156, 158, and 160, respectively, to control the motion of cylinder rods 156c, 158c, and 160c, respectively. A three-way pneumatic valve 170 allows slow venting of pressure from a first chamber 156a of cylinder 156.

Fluid reservoir 114 includes a number of tanks 172. A multi-position valve 174 mounted to reservoir 114 is used to select a desired tank 172. Fluid reservoir 116 includes a number of tanks 176. A multi-position valve 178 mounted to reservoir 116 is used to select a desired tank 176. Multi-position valves 174 and 178, e.g., eight position face valves or tapered plug valves, can also be positioned to connect flow path 190 to atmosphere.

Pressure regulators 180, 182, and 184 adjust the pressure to pneumatic cylinders 126, 128, 130, 156, 158, and 160 and to fluid reservoirs 114 and 116, discussed further below. An adjustable relief valve, e.g., a manual spring loaded plunger valve 186 or an electronic, computer controlled valve, adjusts the gas exhaust pressure from cylinder 126 which determines the lower limit of a negative fluid system pressure pulse.

A pressure transducer 188, e.g., a rapid response pressure transducer such as the strain gauge type transducer 56 described previously, connected to reaction vessel 102 monitors the sample pressure.

Figure 5A:
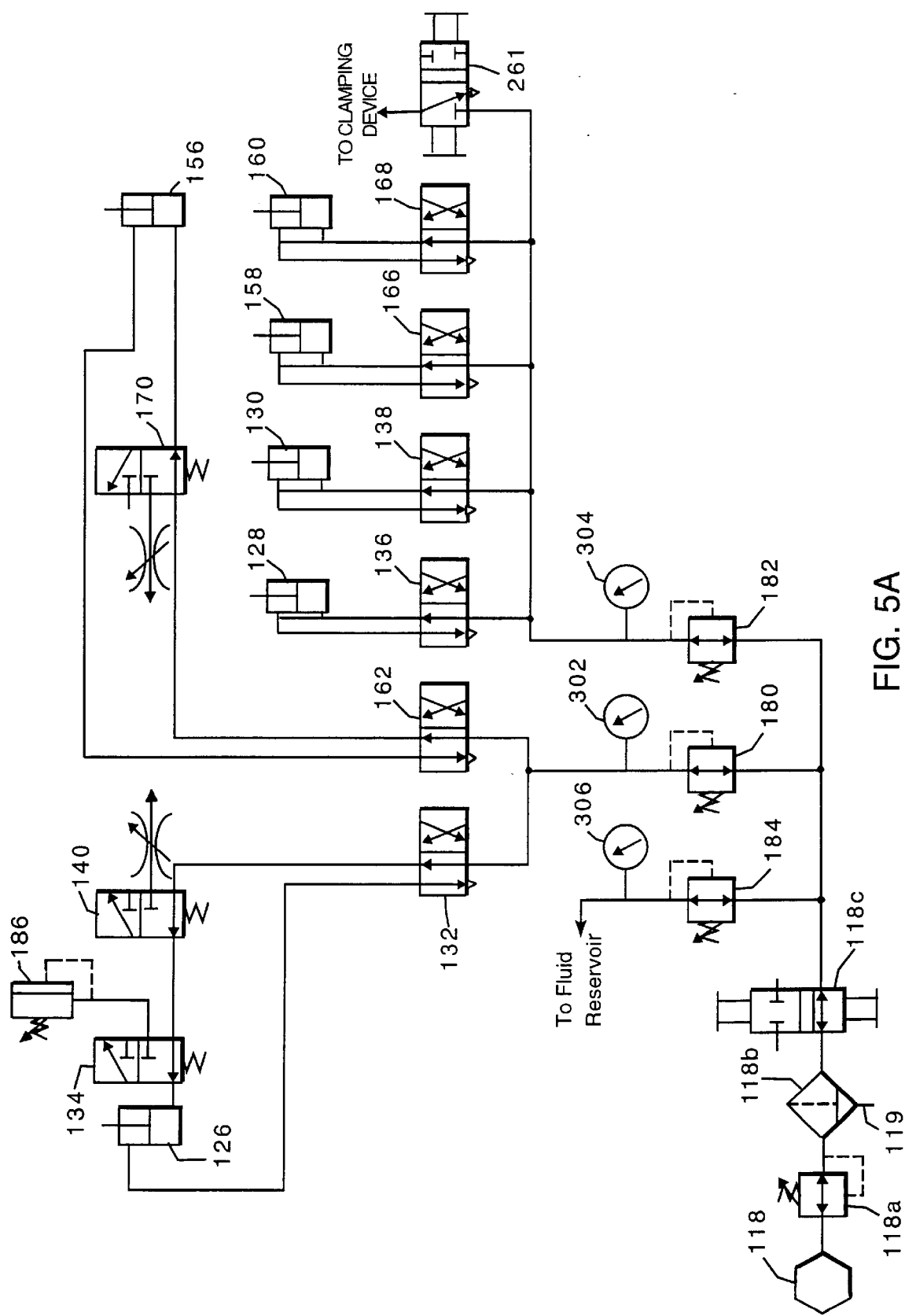
FIG. 5A is a schematic of the hydraulic system of the reactor of FIG. 4.

The pneumatic plumbing is shown in FIG. 5A. Gas from supply 118 is delivered through a pressure regulator 118a, which drops the pressure down to about 200 psi, through a gas filter/water separator 118b having a drain 119, which filters the gas and removes any water from the gas, and through a master valve 118c to regulators 180, 182 and 184. Gas flowing through regulator 180 pressurizes cylinders 126 and 156; gas flowing through regulator 182 pressurizes cylinders 128, 130, 158 and 160; and gas flowing through regulator 184 pressurizes fluid reservoirs 114 and 116. Valves 132 and 162 control which chambers of cylinders 126 and 156, respectively, are pressurized. Valves 136, 138, 166, and 168 control which chambers of cylinders 128, 130, 158, and 160, respectively, are pressurized.

Pressure to the pump pneumatic cylinders 126 and 156 can be set in the range of about 50–150 psi which enables the inhibition pressure in the reaction chamber to be set in the range of about 20,000–60,000 psi. Pressure regulator 182 is set to deliver about 150 psi to valve cylinders 128, 130, 158 and 160. As discussed previously, the reservoir pressures are set at about 10 psi. The pressure regulators can be manually adjustable or computer controlled.

Figure 6:
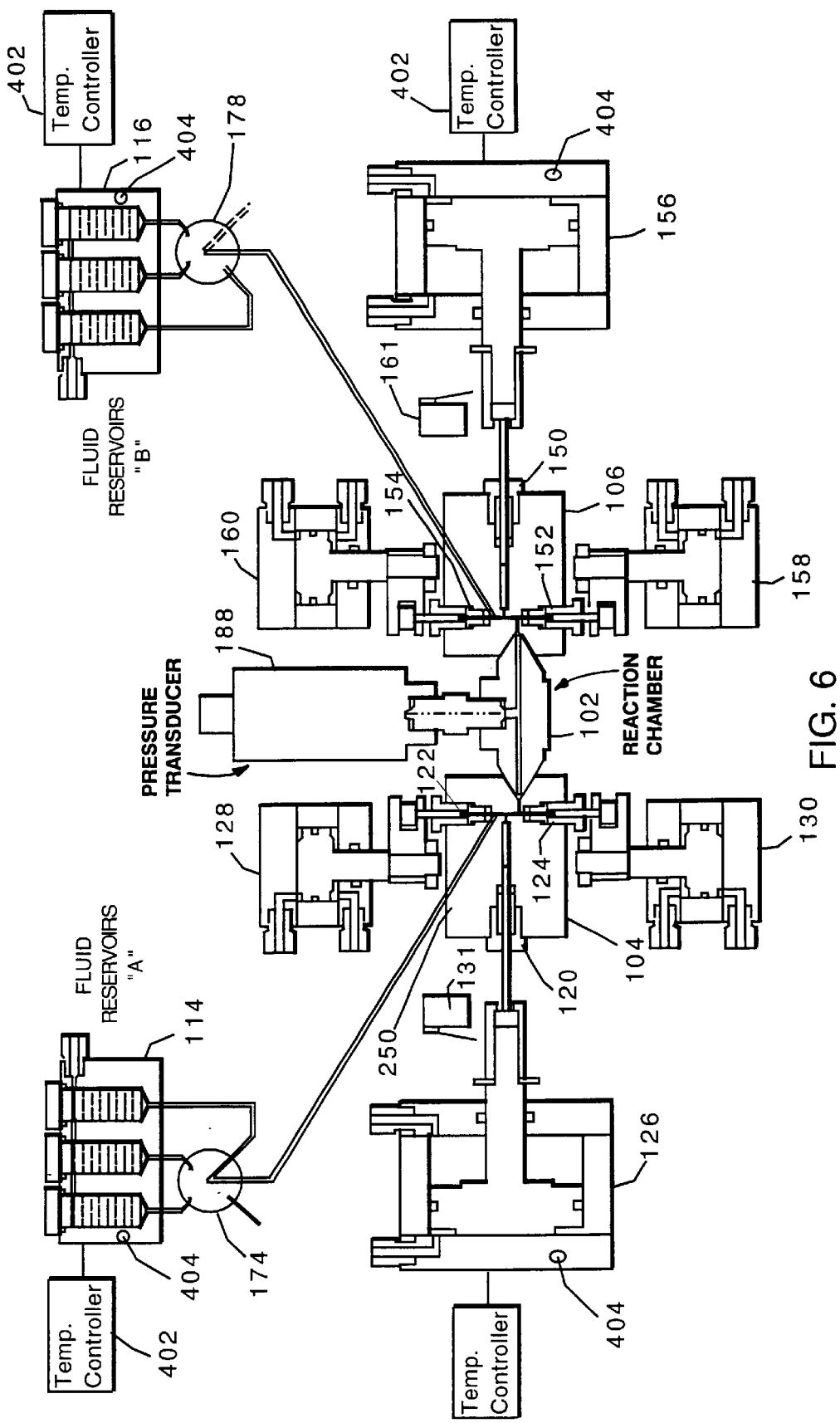
FIG. 6 is a mechanical schematic of the reactor of FIG. 4.

Referring to FIG. 6, the mechanical configuration of pump/valve modules 104 and 106, and cylinders 126, 128, 130, 156, 158, and 160 are shown. The configuration on one side of reaction vessel 102 is a mirror image of the configuration on the other side of the reaction chamber and only pump/valve module 104 and cylinders 126, 128, and 130 are described. Pump 120 driven by cylinder 126, valve 122 actuated by cylinder 128, and valve 124 actuated by cylinder 130 are mounted within a housing 250 of pump/valve module 104.

Figure 6A:
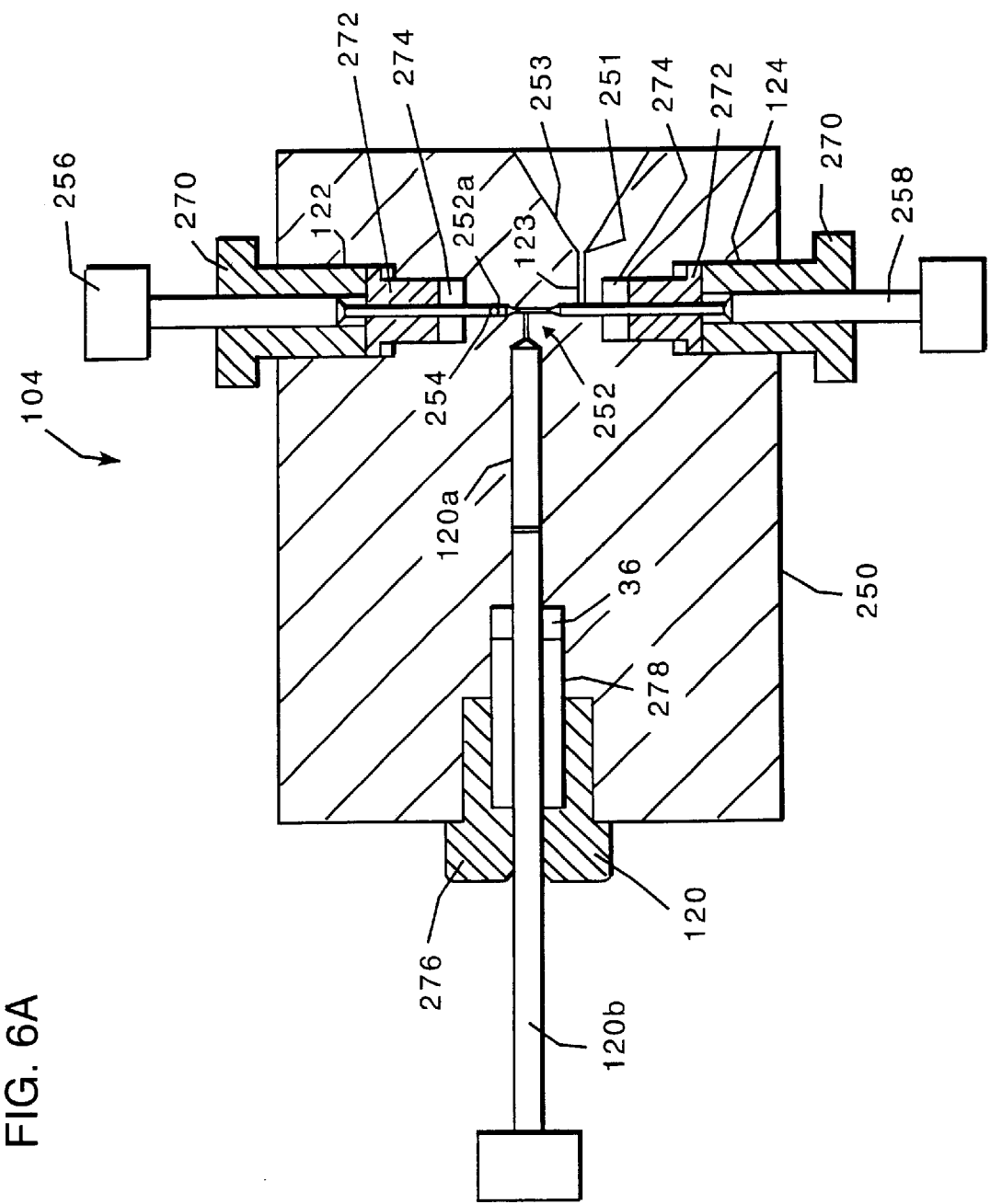
FIG. 6A is a detailed view of a pump/valve module.

Referring to FIG. 6A, housing 250 includes fluid paths 252 defined by conduits 121 and 123 (FIG. 5) and a fluid inlet 254 in an arm 252a of conduit 121. Valve 122 includes a valve plunger 256 which moves between an extended position blocking fluid inlet 254 and a retracted position allowing the flow of fluid through inlet 254. Valve 124 includes a plunger 258 which moves between an extended position blocking flow in conduit 123 leading to reaction vessel 102 and a retracted position allowing flow to the reaction chamber. Piston 120b of pump 120 is used to pressurize fluid paths 252. A fluid outlet 251 of conduit 123 leads to a reaction chamber seat 253 defined by housing 250.

Housing 250 is made from, e.g., stainless steel. Plungers 256 and 258 of valves 122 and 124 are made from, e.g., heat treated stainless steel. Valves 122 and 124 include a packing compression nut 270 made from, e.g., stainless steel, a packing spacer 272 made from, e.g., a bronze alloy, and valve plunger packing disc 274 made from, e.g., teflon. Piston 120b of pump 120 is made from, e.g., heat treated stainless steel. Pump 120 includes a retaining nut 276 made from, e.g., stainless steel, a seal spacer 278 made from, e.g., a bronze alloy, and a piston seal 36 (see FIG. 1A). A pump cylinder 120 is defined by a bore in housing 250.

Figure 6C:
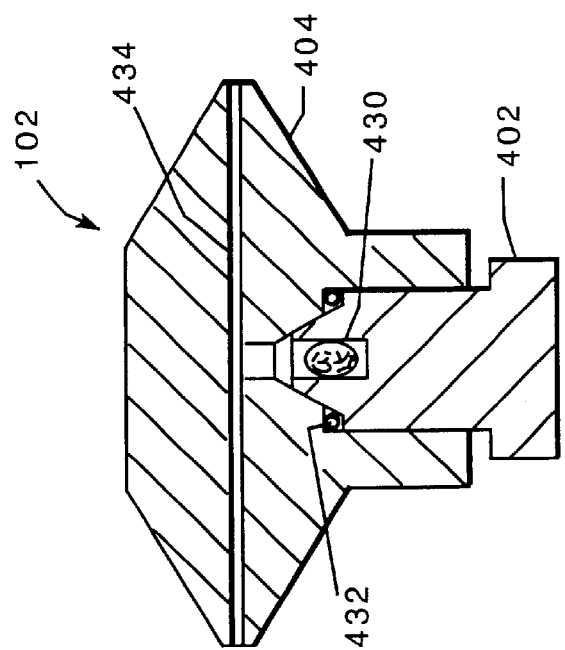
FIGS. 6B and 6C show configurations of reaction vessels.
Figure 6B:
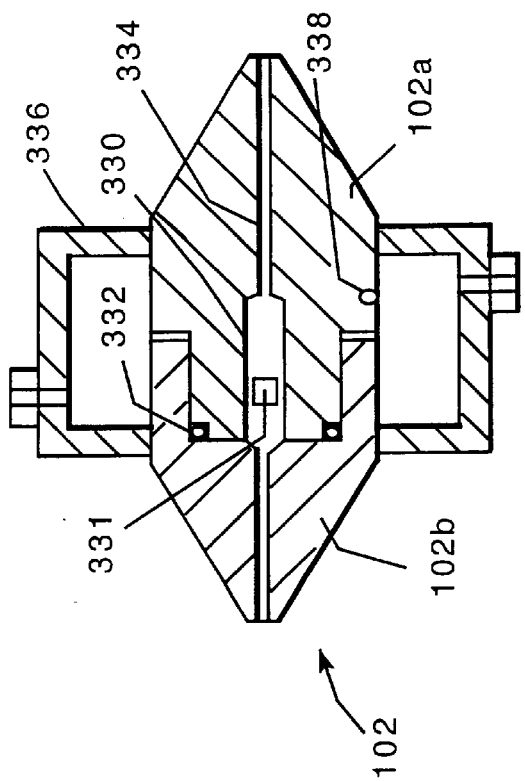

Referring to FIGS. 6B and 6C, various sizes and types of reaction chambers may be utilized, depending upon the nature of the sample and the reaction. As shown in FIG. 6B, reaction vessel 102 includes a first section 102a defining a sample chamber 330, and a second section 102b. Sample chamber 220 can accommodate sample volumes up to several hundred microliters. The two sections are threadedly engaged and sealed with an o-ring seal 332. The two sections define a flow path 334. FIG. 6C shows a configuration of a reaction vessel 102 designed for pressure pulsing but not flow through. A first section 402 defines a sample chamber 430, and a second section 404 defines a flow path 434 in communication with sample chamber 430. The two sections are threadedly engaged and sealed with an o-ring seal 432.

Referring again to FIG. 6B, reaction vessel 102 is temperature controlled by a surrounding fluid jacket 336. Alternatively, thermoelectric heating and cooling can be employed or an air bath can be utilized to control temperature. Reactions may be performed at, above, or below ambient temperature. A temperature sensor 338, e.g., a thermo-couple, thermistor, or RTD, monitors the temperature of reaction vessel 102. Pump/valve modules 104 and 106 and reservoirs 114 and 116 also preferably include temperature controllers 402 and temperature sensors 404 for temperature control by one of the above described methods (see FIG. 6).

Figure 7:
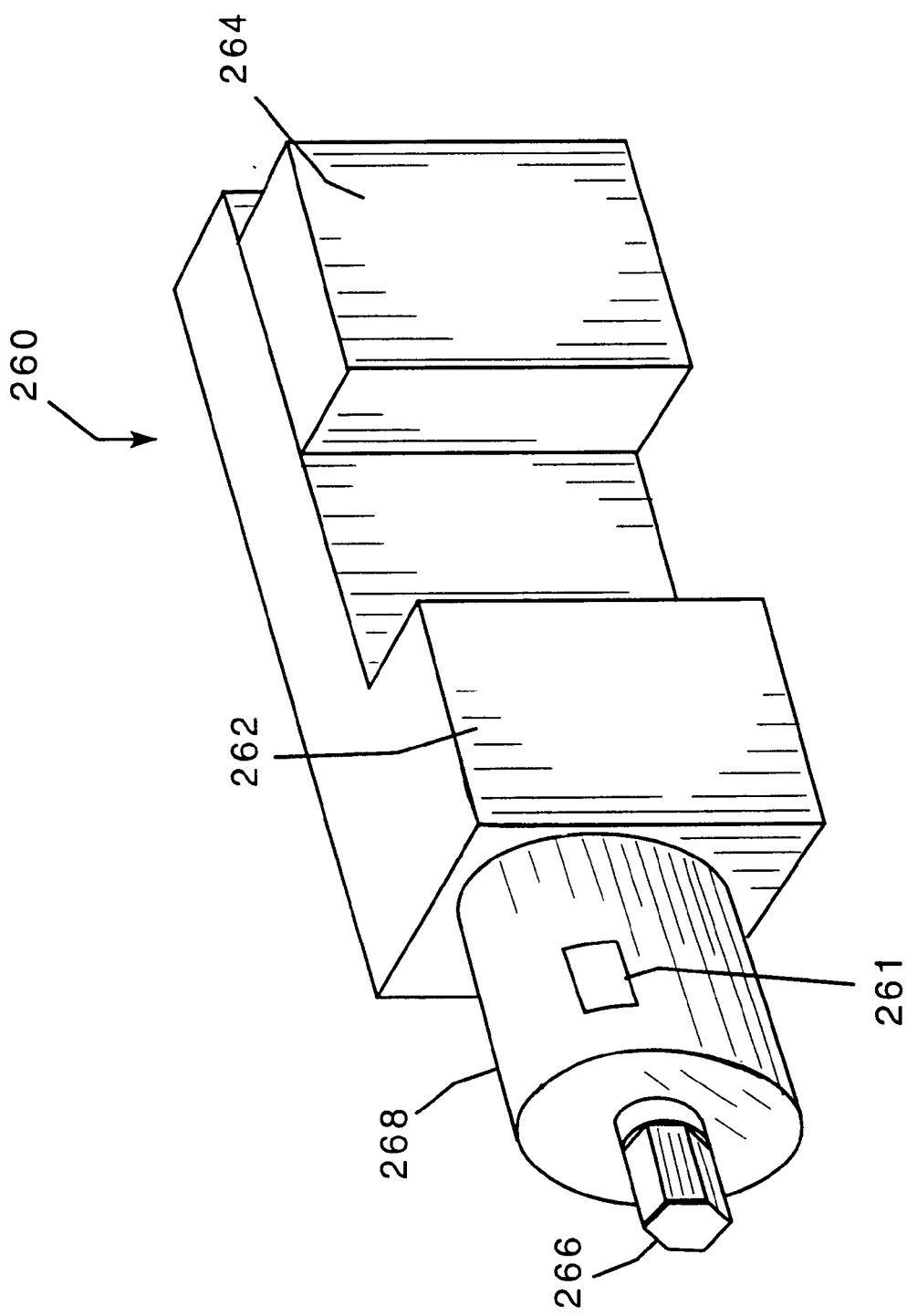
FIG. 7 shows a clamp for sealing the reaction vessel between pump/valve modules.

Referring to FIG. 7, clamp 260 includes a fixed end 262 to which pump/valve module 104, cylinders 126, 128 and 130, and fluid reservoir 114 are mounted, and a movable end 264 to which pump/valve module 106, cylinders 156, 158, and 160, and fluid reservoir 116 are mounted. Reaction vessel 102 is placed between the pump/valve modules, in the reaction chamber seats, and the clamp is tightened to hold and seal the reaction chamber between the modules. Clamp 260 is an air clamped machine vise with large adjustments made manually with a machine screw (hex shaft 266) and final clamping accomplished with a multi-stage, tandem air cylinder 268. Air from regulator 182 controls the clamp air cylinder by passage through a pneumatic on/off valve 261, a manual valve which applies pressure to the clamping cylinder. The maximum clamping force is about 5,000 pounds. This clamping scheme provides for the versatility of being able to rapidly exchange reaction vessel 102 and allowing for reaction chambers of varying sizes.

Figure 8:
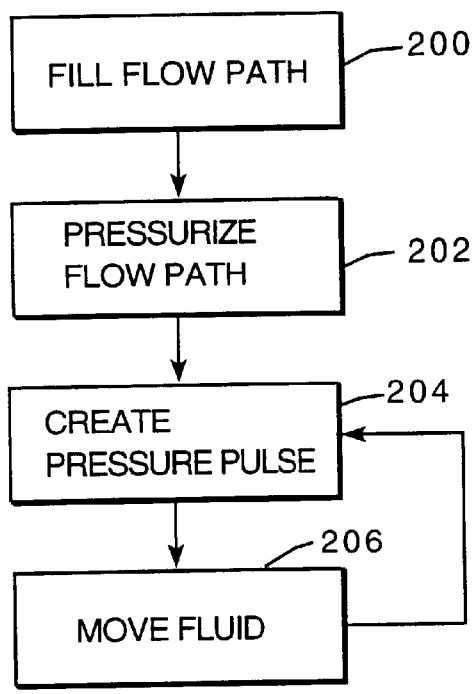
FIG. 8 is a block diagram of the fluid control algorithm.

In use, with a sample to be reacted placed in reaction vessel 102 and the reaction chamber installed in the flow path, fluids generally flow from fluid reservoir 114, through high pressure valves 122 and 124, through reaction vessel 102, through high pressure valves 152 and 154, and exit through valve 178. However, system symmetry also provides for similar flow in the opposite direction. Referring to FIG. 8, the flow of fluid through flow path 190 (FIG. 5) includes first filling the flow path with fluid at 200, pressurizing the flow path at 202, and alternating between creating a pressure pulse at 204 in reaction vessel 102 and moving fluid through the reaction chamber at 206.

Referring to FIG. 9, to fill flow path 190 with fluid, an aliquot of fluid from reservoir 114 is drawn into variable volume pressure chamber pump cylinder 120a of pump 120 by closing valves 124, 152, and 154, opening valve 122, and retracting piston 120b of pump 120 by means of cylinder 126 (step 1). To flow this aliquot through the reaction chamber, valve 122 is closed, valves 124, 152, 154 are opened, and valve 178 is placed in its drain position. Piston 120b of pump 120 is then extended and the contents of pump cylinder 120a expelled through the reaction chamber (step 2). This operation fills fluid path 190 between valves 174 and 178. This is necessary before reaction vessel 102 may be pressurized.

Pressurization of the reaction chamber is performed as follows. Valves 124, 152, and 154 are closed, and valve 122 is opened. Piston 120b of pump 120 is then retracted filling pump cylinder 120a with fluid from reservoir 114 (step 3). Valve 122 is now closed, cylinder 126 is pressurized to extend piston 120b of pump 120, and valve 124 is opened (step 4). Piston 120b of pump 120 will move inward only slightly due to the incompressibility of the fluid in flow path 190. Reaction vessel 102 is now pressurized; the pressure level is a function of the gas pressure setting of regulator 180.

A brief pressure pulse may be generated within the reaction vessel 102 by producing a brief reduced pressure pulse using pump 120. For pressure pulsing, with valves 122 and 152 closed, valve, 124 opened, and piston 120b extended, valve 134 is momentarily actuated (step 5) to open a flow path 134b to vent the pressurized side (chamber 126a) of cylinder 126 to atmosphere through relief valve 186, and then returned to its original flow position allowing flow along path 134a to re-pressurize chamber 126a (step 6). During the venting interval, fluid pressure on piston 120b causes the piston to retract a sufficient amount, to relax the fluid pressure in reaction vessel 102. However, relief valve 186 will limit how low the gas pressure in cylinder 126 can drop, which in turn limits how low the fluid pressure in reaction vessel 102 can drop. Thus, the setting of relief valve 186 establishes a base level for the negative going pressure pulse. When gas pressure is re-applied to cylinder 126, the reaction chamber is restored to its previous pressure level.

To move fluid from pump cylinder 120a to and through reaction vessel 102, while retaining reaction vessel 102 under pressure, cylinder 156 is pressurized driving piston 150b of pump 150 inward (step 7). Valve 152 is then opened (step 8). Due to symmetry, the force on piston 120b will be counterbalanced by the force on piston 150b, and no fluid flow will occur. By switching valve 170 to its vent position, the pressurized end 156a of cylinder 156 is allowed to slowly vent to atmosphere, through the orifice. As the gas is released, piston 120b will extend at a slow rate, and piston 150b retracts. The fluid contained in pump cylinder 120a is transferred through reaction chamber 120 and into pump cylinder 150a of pump 150. Shortly before piston 120b bottoms out, position sensor 131 is activated, delivering an electrical signal which closes valve 152 and switches valve 170 to close the vent port and re-apply pressure to pump 150 (step 9). Note that the reaction chamber pressure continues to be maintained by pump 120.

The fluid contained in pump cylinder 150a is expelled by opening valve 154 and allowing the fluid to drain through valve 178 (step 10). Just before piston 150b bottoms out, sensor 161 sends a signal to close valve 154. Piston 150a continues to extend to pressurize the fluid in conduits 153 and 151 between pumps 154 and 152. The next fluid transfer cycle is then initiated by opening valve 152 and closing valve 124 (step 11). The reaction chamber pressure is now maintained by pump 150. Pump 120 is now ready to again be filled with reagent from fluid reservoir 114. To create another pressure pulse, valve 122 is opened and piston 120b is retracted, then valve 122 is closed, valve 124 is opened, valve 152 is closed, and the process can be repeated from step 4.

It may, for certain reactions, be desirable to move an aliquot of fluid back and forth through the reaction chamber several times before expelling the excess from the system. This might be the case if improved mixing between sample and reagent is desired. To accomplish this, after reagent has been delivered from pump 120, through reaction vessel 102, and the excess is contained in pump 150, the reagent flow is reversed by opening valves 124 and 152, closing valves 122 and 154, pressurizing cylinder 156 to extend piston 150b, and switching valve 140 to allow gas to bleed from cylinder 126 through the orifice.

If it should be desired for certain reactions that one type of reagent flow in one direction and a different reagent flow in the opposite direction, fluid reservoir 116 is included to provide a fluid source an the normally downstream end of the apparatus.

Figure 10:
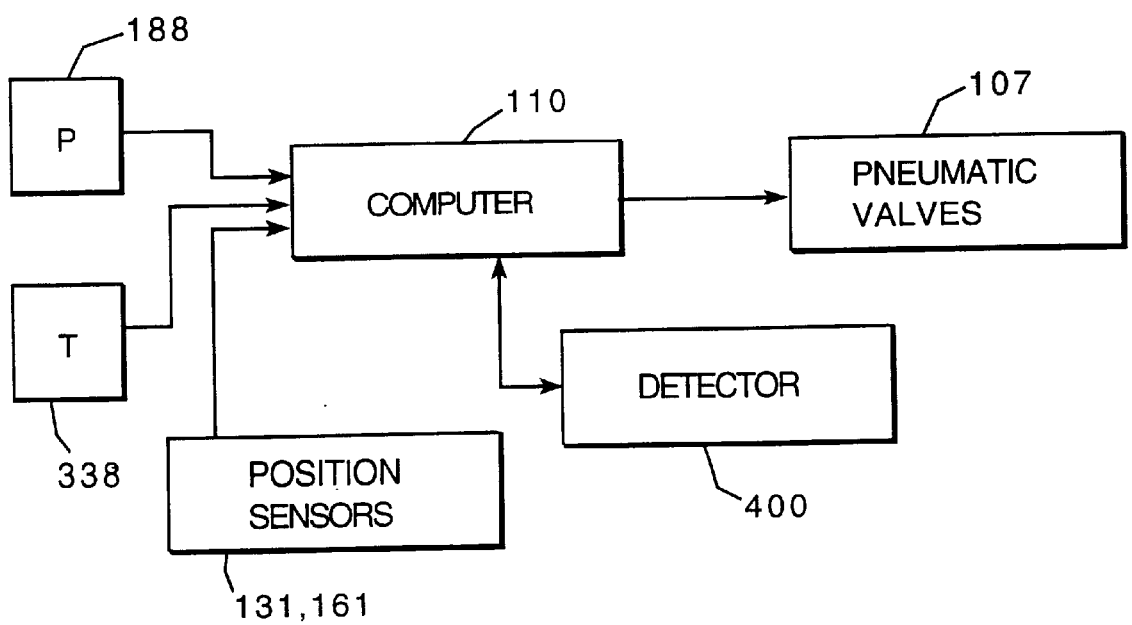
FIG. 10 is a block diagram of the control of the reactor of FIG. 4.
Figure 11:
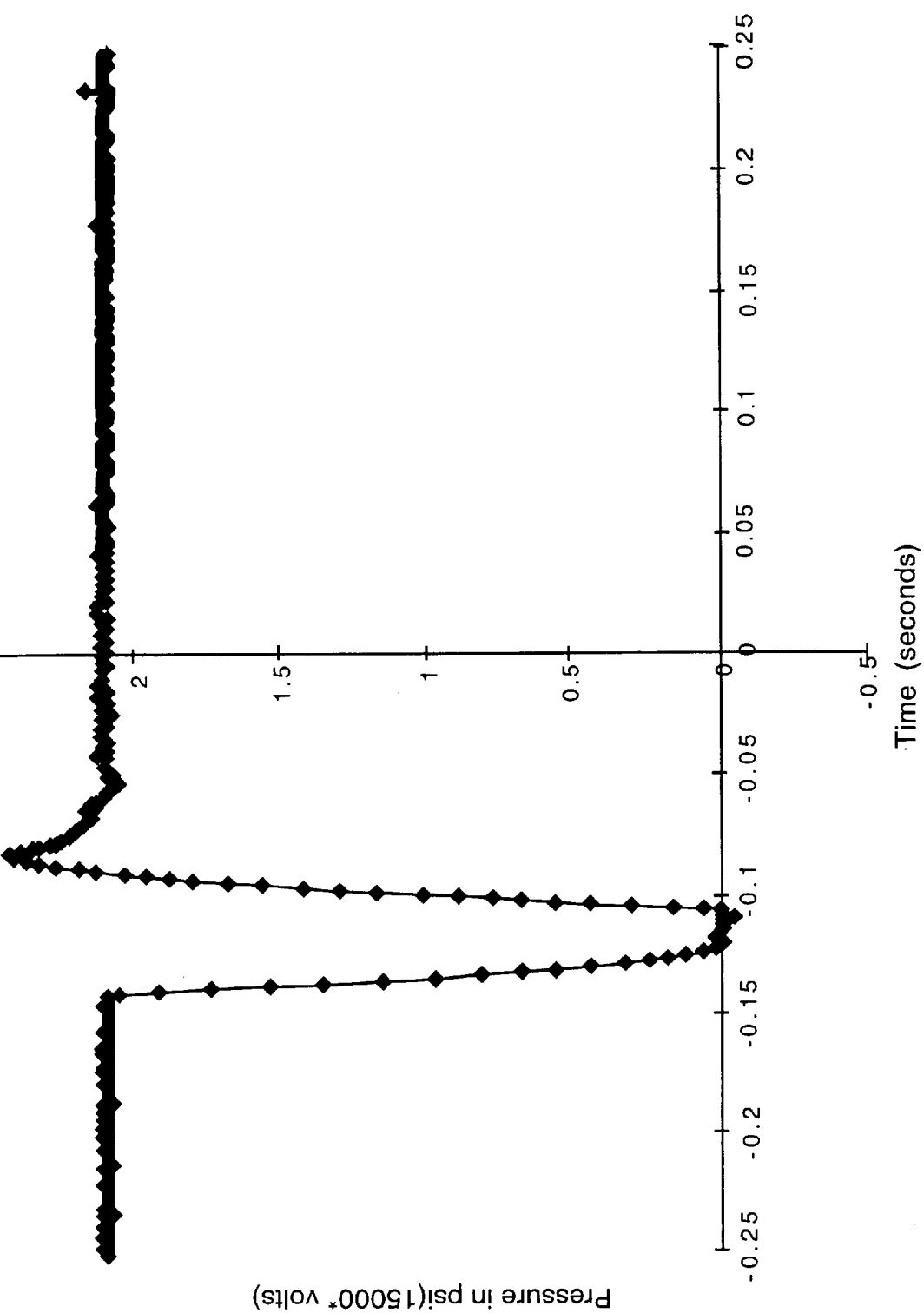
FIG. 11 is a graph showing the pressure-time profile of a pressure pulse.
Figure 12:
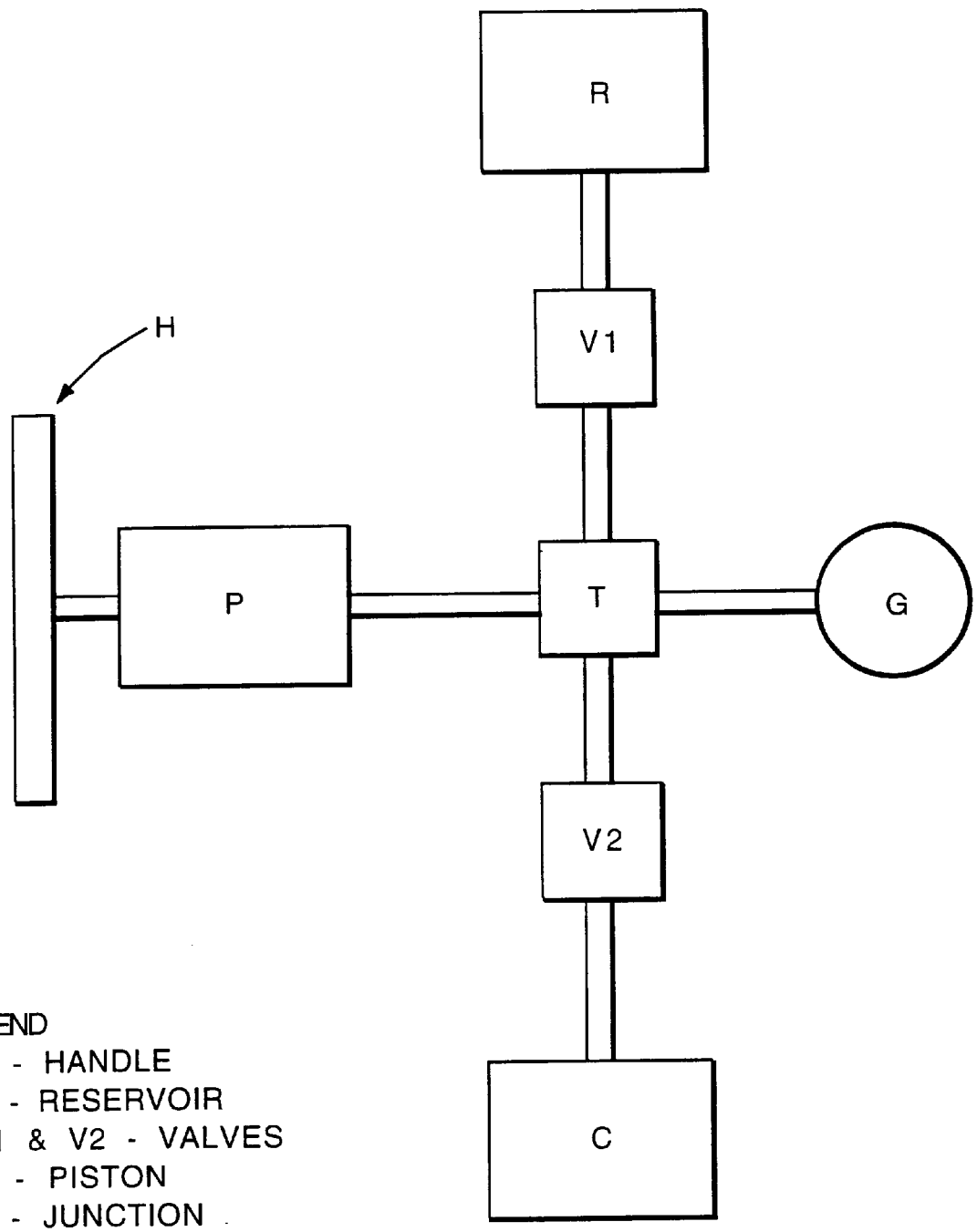
FIG. 12 is a schematic of a device for controlling the action of an enzyme on a nucleic acid substrate by means of applying hydrostatic pressure.

Referring to FIG. 10, the functional components of the fluid system are operated under the control of computer 110. Pressure, temperature and the positions of pistons 120b and 150b as indicated by position sensors 131 and 161 are input to computer 110. Electrical signals to control pneumatic valves 132, 134, 136, 138, 140, 162, 166, 168, and 170 are output by computer 110. Sequencing of fluids and the time-pressure profile are operator programmable. Regulator 180 can be automatically controlled to set the desired pressure levels in the reaction chamber using feedback from the pressure sensor.

C. Uses

The disclosed reactor is used to control chemical reactions including nucleic acid sequencing, nucleic acid synthesis, protein sequencing, enzymatic chiral synthesis, and enantiomeric purification of racemic mixtures. Nonenzymatic reactions can also be controlled.

Desired effects of pressure upon the contents of the reaction vessel include protein unfolding, protein folding, the reversible inhibition of an enzyme, the activation of an enzyme, and shifts in the reaction rate and the thermodynamic equilibrium of nonenzymatic reactions. Pressure-induced inhibition includes inhibiting a single enzymatic reaction step, several sequential enzymatic reaction steps, or the complete enzymatic event. Furthermore, an inhibitory pressure can synchronize the activity of individual reactant molecules (e.g., enzyme, cofactor, or first or second substrate). When the pressure is changed to a permissive pressure, multiple enzyme molecules begin to act at more or less the same time, resulting in more uniform, accurate, and reproducible control of enzymatic activity. A molar excess of enzyme to substrate, if any, usually increases synchronous behavior. Enzymatic reaction steps include the mechanistic steps involved in the reaction between an enzyme (E) and a substrate (S) to form a product (P). Depending on the complete enzymatic event, these steps include conformational change of E, S, P, and combinations thereof; association or dissociation of E-S and E-P; interaction between cofactor and either S or E; interaction among S, E, and a cofactor; solvent interaction with E, S, or a cofactor; proton exchange between E and a component of the sample mixture, such as a S, a solvent, or a cofactor; and a catalytic interaction between E and S. Depending on the enzymatic event, there can be more than one substrate (S, S', S" and so on), more than one product (P, P', P" and so on), and more than one cofactor. Furthermore, some embodiments use more than one solvent or solute (e.g., salt or metal ion) and temperature in conjunction with pressure to provide inhibitory or permissive conditions which control an enzymatic reaction step.

Similarly, changing the pressure of the sample mixture to a pressure which permits an enzymatic reaction step to occur can result in the occurrence of a subsequent enzymatic reaction step, a series of enzymatic reaction steps, or one or more complete enzymatic events. The general method can be used to control enzymatic activity by programming the desired series of single enzymatic events. Hyperbaric treatment causes many biological macromolecules such as proteins, enzymes, antibodies, and polynucleotides which naturally function at pressures of 1 atmosphere to unfold or denature. Such unfolding causes, for example, inhibition of enzyme activity. Conversely, some enzymes or proteins, in particular those which naturally function at high pressures (e.g., in deep sea vent organisms) can be inhibited at lower pressures.

In general, the concentrations, buffers, solvents, enzymes, substrates, and other additives or facilitating molecules are well-known to those in the art. However, higher than usual concentrations of enzyme can be present to achieve more uniform and reproducible results. Those in the art are familiar with commercial sources for nucleic acids, markers, linkers, primers, buffers, amino acids, protecting groups, solvents, enzymes, and other related reagents (e.g., Aldrich, Milwaukee, Wis.; Pharmacia Biotech, Piscataway, N.J.; Promega Corp., Madison, Wis.; Sigma, St. Louis, Mo.; and Stratagene, La Jolla, Calif.)

1. Detection

Where it is desirable to monitor the course of the reaction or the products of the reaction, the pressure cycling reactor includes a detector 400 (see FIG. 10) connected to detect a characteristic of a component present in fluid in or removed from the reaction vessel. The detector can be computer controlled and can relay information regarding the analyzed component to the computer. Thus, components can be analyzed before, during, or after a pressure pulse while in the reaction vessel; components can also be analyzed after being removed from the reaction vessel. Examples of detectors include a radioisotopic detector, an infra-red spectrometer, a mass spectrometer, a gas chromatography-mass spectrometer, a spectrophotometer, a spectrofluorometer, an electrochemical detector, a surface plasmon resonance detector, and a photometer.

2. Reagent Presentation and Product Separation

Reactants can be used efficiently when the pressure cycling reactor has a means for separating reusable or unused reactants from reaction products. The pressure cycling reactor can include a reaction vessel having a restraint 331 (see FIG. 6B) to retain a reagent within the reaction vessel while permitting removal of fluid from the vessel. Examples of restraints include a semi-permeable (i.e., separation) material such as a membrane or matrix which separates the sample mixture components by size, charge, polarity, chirality, or a combination thereof.

The semi-permeable material may occupy a complete cross-section of the sample vessel or the reaction vessel in the manner of a filter or net. The restraint 331, such as a semi-permeable barrier, can divide the reaction vessel into two segments; more than one semi-permeable barrier will divide the reaction vessel into more than two segments.

For example, the reaction vessel or chamber can contain an immobilized substrate retained within the reaction vessel between at least two different membranes. One membrane has pores which allow enzyme and products or small molecules to pass through; another membrane has pores which allow only products or small molecules to pass through.

In addition, the semi-permeable material may be a pouch or bag (whether rigid or flexible) which is attached to the wall of the reaction vessel or the sample vessel. For example, a reaction vessel can include a porous plastic or glass plug with an immobilized reactant or reagent (either enzyme or substrate); or a membrane support on an interior surface of the reaction vessel which supports a porous membrane containing an immobilized reactant. Additional examples include a rigid, hollow porous frit containing an immobilized reagent, wherein the frit is attached to an interior surface of the reaction chamber or vessel. In some embodiments, the restraint can be moved to provide a semi-permeable barrier and then temporarily removed during a programmed series of cycles to allow free flow of all components out of the reaction vessel or a sample vessel.

The separation material is generally chemically inert with respect to the sample mixture components, and structurally resistant to fluid pressures as high as the inhibitory pressures) in a particular application. Size-discriminating membranes or films include DIAFLO® ultrafilter membranes (Amicon, Beverly, Mass.) available in molecular weight cut-offs ranging from 0.5 to 300 kD. For example, membranes can separate enzymes from free nucleotides or amino acids; and immobilized substrates from free enzymes and free nucleotides or amino acids in solution. A separation material such as a membrane or matrix may be impregnated, coated, or otherwise functionalized with a substance or covalently bonded ligand which interacts with a component of the sample mixture. Materials having asymmetric surface properties or asymmetric pore channel hydrophobicity, hydrophilicity, size, and so on may be used. The semi-permeable material can also include analogs of column chromatography, whereby chiral separations are achieved using packed materials through which at least one sample mixture component is eluted.

Depending on the reaction being controlled and the restrictive properties of the restraint selected, the removed fluid can include a nucleotide, an amino acid, an enzyme, an unbound enzymatic substrate, a cofactor, and various solvents or salts. Similarly, the retained components of the sample mixture can also include solvents, salts, enzyme, a free substrate, or an immobilized reagent. An immobilized reagent includes an organic compound attached to a non-liquid support. Examples of a support include polymeric, composite, plastic, or glass beads, matrices, boards or other shapes, including cylinders or tubes.

In some embodiments, the eluted component flows directly into a subsequent sample vessel for additional pressure treatment. The ability to flow fluids at high pressure through the reaction vessel can be used in a method analogous to high-pressure liquid chromatography to assist in separation in addition to controlling enzymatic events.

The separation can occur at any pressure, including high pressure, and at any time with respect to the pressure pulse (i.e., before, during, or after occurrence of one or more enzymatic reaction steps). Separation may occur after each pressure pulse, or after a determined number of pressure pulses.

3. Embodiments

For these reactions, the first and third pressures alone, or in combination with a hypo-ambient temperature, are sufficient to inhibit the activity of the enzyme, while the second pressure alone or in combination with a temperature greater than the first temperature is not inhibitory and thus allows the enzyme to operate on the substrate.

The invention features a method of using the disclosed reactor for sequencing DNA. Restriction endonucleases such as Hind III are distributive enzymes which can be reversibly inhibited by hyperbaric, conditions (see Example 7). Exonucleases for sequencing polynucleo-tides include lambda exonucleases, exonucleases I-III from *E. coli*, nuclease Bal-31, exoribonucleases, and the exonuclease activities of DNA polymerases. For example, exonuclease III is a distributive enzyme that is inhibited at 30,000 psi and at 40,000 psi at 25° C. Based on some detected activity after pressure was reduced, the pressure-induced inhibition is reversible.

According to a method of gene browsing, a region of interest is exposed by restriction endonuclease treatment, and then sequenced. Repeated removal of endonuclease and introduction of a sequencing enzyme allows spot analysis across long nucleic acids without requiring sequencing of the entire polynucleotide. This method of sequence mapping or gene browsing includes providing a sample mixture containing an immobilized large nucleic acid substrate, cleaving the substrate with a restriction enzyme, and removing the restriction enzyme and the cleavage products from the sample vessel. The method further includes adding lambda exonuclease under a lambda exonuclease-inhibiting pressure; changing the pressure to a lambda exonuclease-permissive pressure, thereby detaching a determined average number of nucleotides (preferably 1 nucleotide) from the immobilized nucleic acid; changing the pressure to a lambda exonuclease-inhibiting pressure; and removing and analyzing the detached nucleotide.

Another method of sequencing is confirmatory sequencing. According to this method, a processive lambda exonuclease with 5'–3' activity acts preferentially on double stranded DNA to remove single nucleotides. Afterwards, a processive exonuclease I (magnesium dependent) with 3'–5' activity acts on the now-exposed single stranded DNA to remove single nucleotides. Exo I stops at a double stranded region at or near where the lambda exonuclease was terminated. In this manner, one strand is sequenced, and the complementary'strand is also sequenced to confirm the first sequence.

This method includes providing a sample mixture containing an immobilized nucleic acid substrate, and lambda exonuclease at a lambda exonuclease-inhibiting pressure; changing the pressure to a lambda exonuclease-permissive pressure; changing the pressure to a lambda exonuclease-inhibiting pressure; and removing and analyzing the detached nucleotide(s). After one or more repeated pressure pulses or pressure cycles followed by nucleotide removal and analysis, the lambda exonuclease is eluted from the sample mixture with an eluting solution such as a 0.2–0.5 M NaCl solution, followed by an Exo I buffer, such as 67 mM glycine-KOH, pH 9.5, 10 mM 2-mercaptoethanol, and 6.7 mM $MgCl_2$. The sample vessel is provided with exonuclease I with 3'–5' activity under an exonuclease I-inhibiting pressure; the pressure is changed to an exonuclease-permissive pressure; the pressure is changed to an exonuclease-inhibiting pressure; and a released nucleotide is removed and analyzed.

Additional sequencing methods include both probe sequencing and the sequencing of primer extended probes. Probe sequencing employs single stranded oligonucleotides as primer sets which correspond to known mutation sites (e.g., cystic fibrosis). According to this method, one or more single stranded copies of a patient's DNA is isolated from PCR products and immobilized. Depending on the patient, incubation with known groups of DNA single strand probes results in hybridization of none, one, or more single strand probes, creating a nucleic acid product having double stranded regions of interest. The duplex sections are selectively sequenced by, for example, using a 5'–3' enzyme on a 3'–5' strand.

This method therefore includes providing a sample mixture containing an immobilized single strand PCR amplicon representing the region of interest; adding to the sample mixture a set of oligonucleotides probes encompassing known mutations and wild types; removing unhybridized oligonucleotides; optionally adding a 3'–5' exonuclease; providing a sample mixture containing a lambda exonuclease (5'–3') at a lambda exonuclease-inhibiting pressure; changing the pressure to a lambda exonuclease-permissive pressure; changing the pressure to a lambda exonuclease-inhibiting pressure; and removing and analyzing the released or detached nucleotide(s). The sequencing steps are repeated until the first probe sequence is completed. The next set of probes is hybridized and washed. The single strand is digested with 3'–5' exonuclease until the next double stranded region is reached. Then the lambda exonuclease 5'–3' is used, as above, to analyze the double stranded region. This method can involve fewer operator steps, and is therefore faster than PCR and other amplification techniques.

Using a sequence 5' to a variety of single stranded oligonucleotides corresponding to known mutations in a variable region, the pressure cycling reactor can be used for a method of sequencing primer extended probes. A generic primer probe is incubated with single stranded patient DNA from PCR product, the patient's DNA being isolated and immobilized. Incubation occurs under low stringency conditions to accommodate any mismatches in the generic probe. The probe is extended through the region of interest, and the extended primer is sequenced in the 3'–5' direction with exonuclease III. This sequence analysis detects both known and unknown mutations in the region of interest.

Based on the examples already described, another embodiment of this method can be summarized as follows, since the basic principles of pressure cycling or pressure pulsing have been detailed above. Steps may be combined or split into additional steps. The PCR amplicon of the region of interest is isolated and immobilized; oligonucleotide primer is incubated with the immobilized amplicon; unhybridized probe is removed by washing or elution; nucleotides and DNA polymerase (e.g., $Vent_R$™, New England BioLabs) are provided to the sample mixture under inhibitory pressure; employ pressure pulses to add a determined number of nucleotides to the primer; free polymerase and nucleotides are removed by washing; exonuclease III is provided to the sample mixture under inhibitory pressure; employ pressure pulses to detach single nucleotides from the extended primer; and remove and analyze released nucleotides.

A method for generating partial digests is described below. Conventional methods require significant sample preparation (cleavage to read-lengths of typically 500 bases, isolation, purification, and mapping); sequencing; and data analysis (gap-filling, resolution of ambiguities). The present method affects each of these three steps, for example, by allowing long template read-lengths (e.g., 2,000, 10,000, 25,000, 50,000 or more bases); controlling the enzymatic reaction during sequencing; and simplifying analysis by releasing and detecting only one nucleotide at a time. Gel electrophoresis is not required. Five thousand bases can be sequenced in less than a few hours (e.g., less than two hours or less than one hour). As a result of the above improvements, the cost per sequenced base is also decreased.

Another embodiment of the disclosed reactor is used for synthesizing DNA. Distributive enzymes such as Eco III and DNA dideoxynucleotidyl exotransferase (terminal transferase, e.g., EC 2.7.7.3) are reversibly inhibited with hyperbaric pressure, and the latter enzyme does not require a template for DNA synthesis. A method of synthesizing DNA includes providing (a) a sample vessel containing an initiator (e.g., primer) immobilized on a support (e.g., bead, matrix, or surface); (b) downstream from the immobilized initiator, a semipermeable material with a molecular-weight cut-off sufficient to separate the enzyme from free nucleotides (e.g., 5, 10, 15, 20, or 25 kD). The sample vessel also contains an excess of terminal transferase (e.g., at least 2 mole equivalents per mole of 3' ends of initiator). A solution containing a nucleotide is added to the sample mixture under a terminal transferase-inhibiting pressure. The pressure is changed to a terminal transferase-permissive pressure which is maintained for a length of time sufficient for the incorporation of a determined average number of nucleotides per primer (e.g., one nucleotide per primer, or a single complete enzymatic event). After changing the sample vessel pressure to a terminal transferase-inhibiting pressure, the unincorporated or free nucleotides are washed out of the sample vessel (maintaining an inhibitory pressure), while the enzyme is retained within the sample vessel by the semi-permeable material. The next desired nucleotide is added to the sample mixture, and the cycle is repeated until the desired oligonucleotide is formed.

In some combinatorial embodiments, the sample vessel can contain different immobilized initiators, which are intended to share a oligonucleotide sequence segment which is added simultaneously, a nucleotide at a time, to each of the different initiators. The semi-permeable material can be presented as a downstream barrier or the sample vessel may contain a plurality of molecular weight cut-off pouches made of semi-permeable material, wherein the pouches contain an amount of terminal transferase and one or more primers. Polymerases useful for synthesizing polynucleotides include SP6 RNA polymerase, T7 RNA polymerase, T4 DNA polymerase, E. coli DNA polymerase, sequenase (Sequenase version 2.0 available from U.S. Biochemical Corp, city/state), thermostable DNA polymerases, Tth DNA polymerase, Taq polymerase, Thermococcus sp. (strain 9° Nm) DNA polymerase, Thermococcus litoralis DNA polymerase, and Pyrococcus sp. GB-D DNA polymerase.

Enzymes, in the class E.C. 2.7.7. include nicotinamide-nucleotide adenylyltransferase, FMN adenylyltransferase, pantetheine-phosphate adenylyltrans-ferase, sulfate adenylyl transferase, sulfate adenylyl transferase (ADP), DNA-directed RNA polymerase, DNA-directed DNA polymerase, UTP-glucose-1-phosphate uridylyltransferase, UTP-hexose-1-phosphate uridylyltransferase, UTP-xylose-1-phosphate uridylyltransferase, UTP-glucose-hexose-1-phosphate uridylyltransferase, mannose-1-phosphate guanylyl-transferase, ethanolamine-phosphate cytidylyldtransferase, cholinephosphate cytidylyltransferase, nicotinate-nucleotide adenylyltransferase, polynucleotide adenyltransferase, tRNA cytidylyltransferase, mannose-1-phosphate guanylyltrans-ferase (GDP), UDP-N-acetaylglucosamine pyrophosphorylase, glucose-1-phosphate thymidylyltransferase, tRNA adenylyl-transferase, glucose-1-phosphate adenylyltransferase, nucleoside-triphosphate hexose-1-phosphate nucleotidyltrans-ferase, hexose-1-phosphate guanylyltransferase, fucose-1-phosphate guanylyltransferase, galactose-1-phosphate thymidylyltransferase, glucose-1-phosphate cytidylyltrans-ferase, glucose-1-phosphate guanylyltransferase, ribose-5-phosphate adenylyltransferase, aldose-1-phosphate adenylyl-transferase, aldose-1-phosphate nucleotidyltransferase, 3-deoxymannooctulosonate cytidylyltransferase, glycerol-3-phosphate cytidylyl-transferase, D-ribitol-5-phosphate cytidylyltransferase, phosphatidate cytidylyltransferase, glutamate-ammonia-ligase adenylyltransferase, acylneuraminate cytidylyltransferase, glucuronate-1-phosphate uridylyltransferase, guanosine-triphosphate guanylyl-transferase, genatamicin 2"-nucleotidyltransferase, strepto- mycin 3"-adenylyltransferase, RNA-directed RNA polymerase, RNA-directed DNA polymerase, mRNA guanylyl-transferase, adenylylsulfate-ammonia adenylyltrans-ferase, RNA uridylyltransferase, ATP adenylyltransferase, phenylalanine adenylyltransferase, anthranilate adenylyl-transferase, RNA nucleotidyltransferase, N-methylphospho-ethanolamine cytidylyltransferase, (2,3-dihydroxybenzoyl)-adenylate synthase, and [Protein-PII]uridylyltransferase.

The invention features a similar method for the synthesis of RNA, wherein, for example, the distributive properties of the enzyme polyribonucleotide phosphorylase is substituted for the DNA dinucleotidyl exotransferase or other terminal transferase above. Polyribonucleotide phosphorylase also does not require a template. Numerous other transferases and phosphorylases can be substituted in the above methods. Where an enzyme requires a template, the initiator would include a template.

Polypeptides can be synthesized and sequenced in an analogous manner. Proteolytic enzymes include trypsin (S. aureus extracellular protease), chymotrypsin, pepsin, aminopeptidase M (EC 3.4.11.2), and carboxypeptidases A, B, and C (EC 3.4.17.1; EC 3.4.17.2; and EC 3.4.16.1, respectively). Polypeptides can be synthesized using enzymes such as subtilisin and thermolysin.

4. Synthetic Chemistry

Organic synthesis employs both microbes and enzymes to synthesize chiral compounds. Examples of such enzymes include proteases, dehydrogenases, oxidases, and transferases. Enzymes useful for separation of enantiomers from a racemic mixture include lipases, esterases, proteases, dehydrogenases, oxidases, and transferases.

In principle, the reaction rate of any chemical reaction having a pressure-sensitive transition state can be controlled (increased, decreased, or even stopped) with the brief pressure pulses provided by the disclosed reactor. Examples of chemical reactions include nonenzymatic synthesis of polypeptides, glycoproteins, lipopoly-saccharides, and enzymatic or nonenzymatic synthesis of small chiral molecules. Nonenzymatic reactions are subject to pressure-sensitive thermodynamic equilibria, wherein production of a particular stereoisomer is favored under certain pressures. The equilibria can be based on molar volumes of reactants, transition state complexes, products, or a combination thereof. Where a catalyst is employed, pressure pulses (in combination with temperature) can be used to inhibit or facilitate dissociation of the product from the catalyst, whereby the non-reacted reagents can be separated from the catalyst-product complex, isolating the product and facilitating purification. In some embodiments, ultrasound can generate pressure, pulses.

The invention provides a method of affecting a reaction equilibrium which includes providing an immobilized reagent in a sample vessel at a pressure, introducing one or more reactants under desirable temperature and pressure conditions (e.g., elevated pressure). The reaction proceeds under equilibrium-selective conditions, thereby favoring the synthesis of a particular stereoisomer. The reaction product is removed either at high pressure, or after the sample vessel pressure is reduced.

The disclosed reactor is also useful in modifying compounds by first altering their secondary, tertiary, or quaternary structural conformation. For example, treatment with high pressure exposes one or more amino acid residues which are normally buried (not exposed on the protein surface) as a result of protein folding. After modification of the exposed amino acids, the protein is refolded.

5. Inhibition

Inhibition of an enzymatic reaction step includes prevention of any mechanistic step that influences or participates in an enzymatic reaction pathway, such as those steps described herein, to achieve the completed enzymatic event. Reversible inhibition of an enzymatic reaction step means that under subsequently imposed favorable conditions, the enzymatic reaction step will occur, i.e., that the enzyme has not been irretrievably denatured, irreversibly bonded, altered, or otherwise inactivated. Reversible inhibitory conditions temporarily arrest or hold in abeyance the enzymatic reaction mechanism pathway at a step. Depending on the enzymatic event, the same inhibitory conditions may effectively arrest more than one enzymatic reaction step along the mechanistic pathway. Inhibition of an additional enzymatic reaction step can occur when a condition, such as pressure, temperature, or solvent content, is changed. Depending on the sample mixture and sample mixture conditions such as temperature, inhibition of an additional enzymatic step resulting from a change in pressure can be inhibition of a subsequent single enzymatic reaction step, inhibition of several enzymatic steps, or inhibition of a complete enzymatic event (e.g., cleavage or addition of a nucleotide or an amino acid, or a synthetic organic transformation of a functional group). Once the inhibitory pressure is changed to a permissive pressure, the progress along the enzymatic reaction pathway is limited by sample mixture components, time, temperature, and solvent conditions.

Where all necessary sample mixture components (such as substrate, cofactors, and metal ions) are, present and other conditions such as temperature are favorable, an inhibitory pressure can inhibit the complete enzymatic event. In this case, subsequently changing the inhibitory pressure to a permissive pressure and maintaining the permissive pressure for a sufficient length of time will result in completion of the enzymatic event. Given sufficient time and amounts of sample mixture components, multiple enzymatic events will occur.

Where some but not all necessary sample mixture components and conditions are present, an inhibitory pressure can inhibit one or more of the enzymatic reaction steps. In this second case, subsequently changing the inhibitory pressure to a permissive pressure and maintaining the permissive pressure for a sufficient length of time will result in the occurrence of as many enzymatic reaction steps for which the necessary sample mixture components and conditions are available. Where some of the necessary sample mixture components are absent or conditions such as temperature are unfavorable, the complete enzymatic event cannot occur. However, the sample mixture components and conditions may allow one or more subsequent enzymatic reaction steps to occur.

In one embodiment, the invention contemplates modifying multiple copies of the same DNA fragment using the synchronized action of nucleic acid synthesizing or degrading enzymes. Controlling the period of time that the enzyme is at a permissive pressure governs the number of enzymatic events that act upon and modify the nucleic acid.

One embodiment is a method for treating nucleic acid, comprising: a) providing i) a nucleic acid substrate (e.g., a double-stranded deoxyribonucleic acid substrate), ii) an enzyme capable of acting processively on said nucleic acid substrate (e.g., an exonuclease) and iii) means for applying pressure; b) mixing said nucleic acid substrate and said enzyme to create a reaction mixture (e.g., under lowered temperatures); and c) treating said reaction mixture with said means for applying pressure under conditions (e.g., high pressure such that said acting of said enzyme on said nucleic acid substrate is controlled (e.g., reversibly inhibited).

Another embodiment includes the additional step of d) treating said reaction mixture with said means for applying pressure under low pressure conditions such that said enzyme acts on said nucleic acid substrate; and optionally the additional step e) repeating steps c and d at least once to create further modified substrates. The method may comprise the step of detecting said modified substrates (i.e., the substrates generated at each step where the enzyme is allowed to act) or detecting the other products of the reaction (the fragment or fragments generated from the substrates).

D. Embodiments Varying Pressure and Temperature

Additional control over the process can be achieved by temperature control. In one embodiment, the present invention contemplates a method for treating nucleic acid, comprising: a) providing, in any order: i) a sample vessel, ii) a nucleic acid substrate, iii) an enzyme capable of acting on said nucleic acid substrate, iv) means for controlling pressure, and v) means for controlling temperature; b) adding said enzyme in an aqueous solution to said sample vessel; c) lowering the temperature of said aqueous solution in said sample vessel with said temperature controlling means such that said enzyme is rendered substantially inactive; d) adding said nucleic acid substrate to said inactive enzyme to create a reaction mixture; e) increasing the pressure to said sample vessel with said pressure controlling means; f) raising the temperature of said reaction mixture in said sample vessel with said temperature controlling means; and g) lowering the pressure in said sample vessel with said pressure controlling means such that said enzyme is active and acts on said nucleic acid substrate. It is contemplated that said increasing the pressure of step (e) achieves a pressure capable of substantially inhibiting said enzyme from acting on said nucleic acid substrate at optimum enzymatic temperatures. It is also contemplated that said acting of the enzyme in step (g) causes said nucleic acid substrate to be modified. The method may further comprise the step, after step (g), of detecting said modified nucleic acid substrate. It is also contemplated that said raising the temperature in step (f) achieves a temperature at which said enzyme is active.

In another embodiment, the present invention contemplates a method for treating nucleic acid, comprising: a) providing, in any order: i) a sample vessel, ii) a nucleic acid substrate, iii) an enzyme capable of acting on said nucleic acid substrate, iv) means for controlling pressure, and v) means for controlling temperature; b) adding said enzyme in an aqueous solution to said sample vessel; c) lowering the temperature of said aqueous solution in said sample vessel with said temperature controlling means to less than approximately 5° C., thereby rendering said enzyme substantially inactive; d) adding said nucleic acid substrate to said inactive enzyme to create a reaction mixture; e) increasing the pressure in said sample vessel with said pressure controlling means to greater than approximately 30,000 pounds per square inch; f) raising, the temperature of said reaction mixture in said sample vessel with said temperature controlling means to greater than approximately 30,000 pounds per square inch; f) raising the temperature of said reaction mixture in said sample vessel with said temperature controlling means to greater than approximately 10° C.; and g) lowering the pressure in said sample vessel with said pressure controlling means to less than approximately 20,000 pounds per square inch, thereby rendering said enzyme active such that said enzyme acts on said nucleic acid substrate. In one embodiment, said lowering the pressure in step (g) achieves a pressure of approximately 5,000 to 15,000 pounds per square inch and said raising the temperature in step (f) achieves a temperature of approximately 15° C. to 20° C.

In still another embodiment, the present invention contemplates a method for treating nucleic acid, comprising: a) adding, in any order, an enzyme in solution to a first sample vessel and a nucleic acid substrate in solution to a second sample vessel; b) lowering the temperature of said first and second sample vessels to between approximately 0° C. and approximately 5° C.; c) combining said nucleic acid substrate and said enzyme in a reaction vessel to create a reaction mixture having a temperature between 0° C. and approximately 5° C., d) increasing the pressure in said reaction vessel with a pressure controlling means; e) raising the temperature of said reaction mixture in said reaction vessel to between approximately 10° C. and approximately 80° C.; and f) lowering the pressure in said reaction vessel with said pressure controlling means such that said enzyme acts on said nucleic acid substrate and causes said nucleic acid substrate to be modified. The present invention further contemplates the step of repeating steps d) and f) at least once to create further modified substrates.

The modification of nucleic acid can be measured by detecting the modified nucleic acid substrate after treatment. Alternatively, the nature and/or extent of the, modification of nucleic acid can be determined by detection and identification of the base added or removed by the enzyme.

In one embodiment, it is contemplated that the synchronized enzyme activity is employed for the generation of nested deletions. By virtue of the use of pressure, the rate of digestion can be finely controlled, allowing for the routine generation of groups of deletions having defined lengths.

It is also contemplated that the present invention can be used with success for nucleic acid sequencing. Moreover, alternative embodiments of the present invention will be useful for protein sequencing, polysaccharide sequencing, and protein synthesis. In one embodiment, the nucleic acid sequencing method is automated. In one embodiment, the present invention contemplates a method for sequencing a double- or single-stranded polynucleotide comprising: a) immobilizing a polynucleotide having a first end; b) introducing a processive enzyme capable of binding to said first end so that binding occurs; c) applying a hydrostatic pressure capable of inhibiting the said enzyme; d) decreasing said hydrostatic pressure to a non-inhibitory level for a time interval that allows said enzymes to act on said polynucleotide to generate a product; e) transporting said product to a detector by applying a high pressure flow stream; f) detecting said product with said detector; and g) repeating steps (c) through (f) so that said enzyme translocates the complete length of said polynucleotide. It is contemplated in one embodiment that said polynucleotide is single stranded and steps (d) through (g) occur synchronously for a plurality of said single stranded polynucleotides.

The method may be performed and the immobilization may be carried out in the reaction chamber. In one embodiment, the immobilizing comprises hybridizing said polynucleotide to a complementary fragment-covalently bound to said reaction chamber. The enzyme may be a DNA polymerase and it may be introduced by pumping (along with a first deoxynucleotide triphosphate) into said reaction chamber.

It is not intended that the invention be limited by the method of detection. For example, the detector might be a mass spectrometer or fluorometer.

The invention relates to controlling the activity of an enzyme and, more particularly, to using synchronized enzyme activity to treat a substrate such as nucleic acid. This novel approach rests on the ability to precisely control the activity of an enzyme involved in the synthesis or degradation of DNA by applying high hydrostatic pressure to the reaction system interrupted by pulses of low pressure. The ability to precisely control the activity of multiple copies of the enzyme, each bound to a strand of DNA (e.g., immobilized DNA), results in synchronous rounds of the enzyme-catalyzed reaction. During each round, sufficient soluble product is formed to be detected when the product is transported in a buffer stream to a detector. For example, exonucleases are synchronized so that many enzymes working on multiple copies of DNA all move forward and release the same base at the same time. Conversely, DNA polymerases would all move forward and add the same base. The reaction products are readily detected using available technology such as electrochemical detection, mass spectrometry and fluorescence spectroscopy.

E. Enzymes

The present invention contemplates the use of enzymes having processive properties and enzymes having nonprocessive (distributive) properties. By changing salt or ion conditions, some enzymes can have either processive or distributive properties (e.g., certain phosphorylases). A processive enzyme is one that repeatedly catalyzes chemical reactions while it remains bound to and moves along a particular substrate. In one embodiment, the present invention contemplates controlling, in single base increments, the movement of a processive enzyme along a DNA template. This is accomplished by applying high hydrostatic pressure to the reaction system to arrest or inhibit enzyme activity. Subsequently, a change (e.g., decrease) in the hydrostatic pressure is applied for a brief interval to allow the enzyme to move along the DNA template to an adjacent base. This movement is defined herein as translocation of the DNA along the enzyme.

In one embodiment, enzymes employed in the method of the invention exhibit high processivity. While monomeric enzymes are preferred, oligomeric enzymes that do not dissociate under the reaction conditions of the invention are also appropriate. Modification of a secondary reaction parameters such as temperature, pH, salt concentration, and buffer components can reverse the subunit dissociation induced by pressure.

Enzymes useful for sequencing DNA include DNA polymerases and exonucleases. An example of an exonucleases found useful in the present invention is Lambda Exonuclease. This enzyme catalyzes the processive, stepwise hydrolysis and release of 5' mononucleotides form the 5'-phosphoryl termini of double-stranded DNA. See J. W. Little et al., *J. Biol. Chem.* 242:672 (1967). The enzyme is available commercially (e.g., Novagen, Inc., Madison, Wis.).

In selecting appropriate enzymes, those enzymes exhibiting non-typical physicochemical characteristics may be useful. Illustrative examples include but are not limited to (1) enzymes from "vent" organisms such as Pyrococcus species GB-D isolated from a submarine thermal vent at 2,010 meters (Deep Vent®, New England BioLabs) and genetically engineered enzymes endowed with both the ability to tolerate a wider range of reaction conditions and improved sequencing product yield. An example of the latter is Sequenase, which is a genetically engineered (commercially available) version of bacteriophage T7 DNA polymerase having two subunits and no 3'–5' exonuclease activity. Other examples include DNA polymerase form *Thermus thermophilus*, which is a monomeric enzyme having no detectable 3'–5' or 5'–3' exonuclease activities and a wide temperature range. DNA polymerase from bacteriophage T4 is a single polypeptide chain having both 5'–3' and 3'–5' exonuclease activity.

Some exoribonucleases can also be used in accordance with the method of the present invention. These enzymes utilize RNA as a substrate. See N. G. Nossal and M. F. Singer, *J. Biol. Chem.* 343:913 (1968); C. B. Klee and M. F. Singer, *J. Biol. Chem.* 243:923 (1968).

To select appropriate processive enzymes, the behavior of enzymes under specific conditions needs to be determined to address the following questions: (1) Within what pressure range does the enzyme remain stable with and without DNA substrate? (2) At what pressures is the enzyme reversibly inhibited and is this inhibition due to dissociation of the enzyme from the DNA substrate? (3) Does adjustment of reaction parameters during pressurization lead to improvements in enzyme stability and performance? (4) How well is synchronicity maintained as a function of the pressure pulsing rate and what is the estimated rate of enzyme movement along the DNA substrate at the permissive pressures?

As is herein demonstrated, some enzymes tested exhibit a stability profile sufficient for synchronous DNA sequencing. The conditions described herein provide a convenient operating pressure range and duration of pressure pulse appropriate for the particular enzyme.

F. Application of High Pressure

It is not intended that the present invention be limited by the nature of the pressure device. A "manual" instrument system capable of generating pressures of 411 MPa is commercially available; the system uses silicone oil as the pressurizing medium, and has a 2 mL reaction vessel (High Pressure Equipment Company, Erie, Pa.). A schematic of this system is shown in FIG. 1.

In some of the experiments (see below) the-high pressure apparatus was a device having the following components: 1 pressure generator (max pressure 60,000 psi) cat #37-5.75-60; 1 pressure gauge cat #6PG75; 2 valves cat #60-11HF4; 2 tees cat #60-23HF4; 4, ¼"×6" nipples cat #60-8M4-2; 2, ¼"×2¾" nipples cat #60-8M4-1 and 1, 2 ml reaction chamber. A pressure gauge with 5 MPa increments is also connected to the system.

The solutions to be pressurized are placed in small deformable polyethylene capsules that are crimp sealed at the ends. A capsule containing 10 to 50 μl of the enzyme/substrate solution is placed in the reaction vessel, which is then connected to the system and pressurized.

It is contemplated that the pressure feature of the present invention can be combined with the use of temperature. This is useful for, among other things, controlling the enzyme during dead time (e.g., time to mix and load the sample before pressure treatment, and time to unload and remove sample for analysis). In some of the experiments (see below), separate enzyme and substrate solutions are held on ice. The reaction chamber was held in a refrigerator (about 5° C.). Pipet tips, capsule, forceps, razor blade, and working surface (3 glass plates taped together) were all held at −20° C. The capsule was crimped sealed at one end before chilling. All work was done on the −20° C. glass plates. The DNA substrate and enzyme solutions were loaded into the capsule with cold tips. The end of the capsule was then crimped and sealed. (This takes about 5 minutes). The reaction chamber was then connected to the pressure apparatus, and a pressure under which the enzyme is not active was applied (e.g., 50,000 psi). The reaction chamber was brought to the desired temperature. The pressure was then jumped to the desired pressure for the desired time (e.g., 15,000 psi to activate an enzyme), then back to a pressure which stops the enzyme (e.g. 30,000 psi). The reaction chamber was disconnected (under pressure) and placed in a −700 freezer (45 min). The frozen sample was recovered by cutting off the ends of the capsule, then centrifuging the capsule in a microfuge tube containing stop buffer which inhibits further enzymatic reaction. The dead time control was jumped from 50,000 psi to 30,000 psi for the same time period as the reaction at the permissive pressure, then treated the same as the experimental sample.

As indicated above, temperature can be used in conjunction with pressure to control enzyme activity. For instance, Example 4 illustrates how the alteration of temperature can be used to control the rate of enzyme digestion. Under the conditions described in that example, digestion (i.e., the number of bases removed from the DNA sequence per second) proceeds at a rate 10 times greater when the temperature is 20° C. than when the temperature is 15° C. when the pressure at both temperatures is set at 10,000 psi. The fact that a relatively small decrease in temperature (i.e., 5° C.) can cause significant decreases in the rate of digestion provides a researcher with greater control over enzyme activity; this may be especially important during dead time, when it may be advantageous to prevent (to the extent possible without harming the enzyme) the digestion taking place while not under pressure.

G. Automated Sequencing Instrument

The present invention contemplates an automated instrument for sequencing which utilizes precise, rapid and automated changes in hydrostatic pressure to synchronize multiple enzyme-substrate complexes. The instrument couples a high pressure reaction chamber to a high velocity pump and a rapid detector. The instrument is capable of sequencing at a rate of several bases per second and has a read length of 5,000 to 10,000 bases, with the possibility of reinitializing and continuing sequencing on the same immobilized substrate.

An automated instrument based on this technology performs the following steps: (1) immobilize one end of the DNA to be sequenced in a flow chamber; (2) bind enzymes to the DIIA "ends" under conditions where catalysis is limited to no more than one base; (3) reversibly inhibit enzyme activity with high pressure; (4) activate enzymes by briefly decreasing the pressure for a time interval, such that the enzymes synchronously step forward by one base; (5) at an inhibitory pressure, quickly move products to the detector with a high pressure high flow stream; (6) repeatedly cycle through steps (3), (4) and (5).

Three different sets of steps could be used for an automated instrument. The characteristics of the enzyme used for sequencing determine which set of steps would be used. The characteristics of the enzyme would place it in one of the following groups:

A. The pressure used to inhibit catalytic activity does not prevent binding of the enzyme to the substrate.

B. The pressure that inhibits catalytic activity also inhibits initial binding to substrate but does not dissociate substrate bound enzyme. Other conditions can be modulated to control the catalytic activity. These conditions include temperature, pH, ionic strength, the concentration of magnesium ions and other cofactor concentrations.

C. The pressure that inhibits catalytic activity also inhibits binding, and the catalytic activity can not be effectively modulated by other conditions.

An automated instrument based on a group A enzyme would perform the following steps:

(1) immobilize one end of the DNA to be sequenced in a flow chamber; (2) reversibly inhibit the activity of an enzyme solution with high pressure and inject this solution into the flow chamber. (3) allow the enzyme to bind to the DNA and then wash out unbound enzymes; (4) activate enzymes by briefly decreasing the pressure for a time interval, such that the enzymes synchronously proceed through one catalytic event; (5) quickly move products to the detector with a high pressure high flow stream; (6) repeatedly cycle through steps (4 and (5).

An automated instrument based on a Group B enzyme would perform the following steps:

(1) immobilize one end of the DNA to be sequenced in a flow chamber, (2) flow an enzyme solution whose activity is inhibited by some condition other than pressure into the flow chamber, e.g. no free magnesium ions; (3) allow the enzyme to bind to the DNA and then raise the pressure to an inhibitory level; (4) change the inhibitor condition to one that permits activity when the pressure is decreased, e.g. add free magnesium ions; (5) activate enzymes by briefly decreasing the pressure for a time interval, such that the enzymes synchronously proceed through one catalytic event; (6) quickly move products to the detector with a high pressure high flow stream which maintains the active-conditions; (7) repeatedly cycle through steps (5) and (6).

An automated instrument based on a Group C enzyme would perform the following steps:

(1) immobilize one end of the DNA to be sequenced in a flow chamber; (2) reversibly inhibit the activity of an enzyme solution with high pressure and inject this, solution into the flow chamber; (3) activate enzymes by briefly decreasing the pressure for a time interval, such that the enzymes synchronously bind and proceed through one catalytic event; (4) quickly move products to the detector with a high pressure high flow stream; (5) repeatedly cycle through steps (3) and (4). The flow stream should contain enzyme to replace enzyme washed out with the products or a means of retaining the enzyme in the flow cell such as a semi-permeable material should be used.

The instrument contemplated in the present invention comprises a reaction chamber connected to a pump and to a detector. The reaction chamber contains immobilized DNA and is designed with valves for introducing reagents and DNA-binding enzymes. The pump provides a flow of buffer through the system. The pressure pulses, controlled by a means for generating pressure pulses, serve to synchronize the enzymes catalyzing reactions in the reaction chamber. The detector identifies products transported in the buffer outflow from the reaction chamber.

As contemplated in the present invention, modification of the pulsing system used in pressure-jump experiments should be appropriate. One such pulsing system is a hydraulically activated apparatus that can change pressures in six milliseconds (Brower, K. R., (1968) "A method for measuring the activation volumes of fast reversible reactions," *J. Am. Chem Soc.*, 90:5401–5403). A pulsing system that uses piezoelectric transducers and can change pressures in 100$\mu$ nsecond is also appropriate (Clegg, R. M., Elson, E. L. and B. W. Maxfield, (1975) "A new technique for optical observation of kinetics of chemical reactions perturbed by small pressure changes," *Biopolymers*, 14:883–887).

The temperature jump associated with the adiabatic compression of water is 1×10$^{-3}$ deg/atm (Brower, K. R., (1968) "A Method For Measuring The Activation Volumes of Fast Reversible Reactions," *J. Am. Chem. Soc.*, 90:5401–5403).

Several chemical methods for the immobilization of DNA have been described (Goodchild, J., (1990) "Conjugates of Oligonucleotides And Modified Ologonucleotides: A Review Of Their Synthesis And Properties," *Bioconjugates Chem* 1:165–187). Single-stranded DNA can be immobilized by hybridization to a complementary fragment covalently bound to the reaction chamber.

Various detectors are appropriate for use with this system. The types of enzyme used for the sequencing affects the choice of detector.

A. If a DNA polymerase is used in the instrument, then a mass spectrometer of fluorometer could be used as the detector in the following formats:

1. Use of nucleoside triphosphates, that have a modification at the beta or gamma phosphate position. Each nucleoside triphosphate would have a unique modification that allows the mass spectometer to distinguish between the pyrophosphate products generated as the polymerase steps along the template. For example, the pyrophosphate could contain 0, 1, or 2 thio substitutions. This would permit three nucleoside triphosphates to be uniquely-labeled. The fourth could be labeled with a stable isotope such as $^{18}$O or $^{34}$S. A time of flight mass spectrometer would have the speed and sensitivity needed for rapid sequencing.

2. Use of a mass spectrometer detector could also involve having only two of the four dNTPs present in the reaction chamber at the same time. Again a thio group can be incorporated into one of the dNTPs to permit identification of the source of the pyrophosphate product. This format would be slower because it would necessitate washing two different dNTP solutions in and out of the reaction chamber. There are two reasons for choosing this format; a) it would provide an additional control on the polymerase activity; and b) it provides a method for improving the yield of product for each base addition (i.e., it improves the step efficiency). The following strategy could be used to increase step efficiency. The reaction chamber could be pulsed a number of times which would equal the number of times that bases had been added from the current dNTP solution. This would allow the yield for each addition to be improved as the polymerase would be given two chances to add the base. This improvement in efficiency might allow sequencing of nucleic acids containing 10,000 or more base pairs.

3. Yet an additional format would use a fluorometer as the detector. A solution of all four fluorescently labeled dNTPs would be pumped into the reaction chamber. The concentration of the dNTPs in this solution would be below the $K_m$ for the polymerase. This would provide a greater relative change in the concentration of the dNTPs after one of the bases had been added; making it easier to determine which base had been added. The detector could distinguish the different labels either by emission spectra or by fluorescent lifetime. After the detector has identified the base added, a solution of the appropriate unlabeled dNTP at high concentration would be pumped into the reaction chamber and pulsed. This is necessary to ensure a high yield of bases added at that step. Next, the labeled dNTP solution would again be pumped into the reaction chamber and the next base determined.

B. If an exonuclease is used for the sequencing then the substrate is the immobilized DNA, and the products are the nucleoside monophosohates released by the enzyme. Each time the reaction chamber is pulsed the next nucleoside monophosphate would be released. The resultant product would then be pumped to the detector. For example:
1. Again the detector could be a mass spectrometer which would distinguish which base had been released. This format would not require the uses of labeled DNA which would simplify template preparation.
2. Another approach would be to enhance the intristic fluorescence of the dNMPs by lowering the temperature and adding an enhancer such as HCl (Ishikawa, M., (1993) "Superfast Determination of Nucleotides in DNA," Japanese Patent JP 05,126,739 [93,126,739] May 21). This method does not require the use of fluorescently labeled substrate to generate the fluorescent signal.
3. Yet another approach would be to employ electrochemical detection, which can distinguish between the four different dNMPs.

One embodiment of a sequencing instrument operates as follows. Polymerases are bound to the immobilized DNA by pumping enzyme concurrently with the known first dNTP that is added into the reaction chamber. The first base to add is known because either the primer sequence is known, or the sequence of the restriction endonuclease used to linearize the vector is known. The pressure is increased to the arresting level and unbound enzyme and dNTP removed. If the enzyme's polymerizing activity is to be used, then a test solution containing dNTPs is pumped into the reaction chamber and a decreasing pressure pulse applied. Alternatively, if the enzyme's 3'–5' exonuclease activity is to be used, then pressure pulsing begins after the dNTP is washed out. If an exonuclease binding to a single-stranded DNA is the elected method of sequencing, then the enzyme is pumped into the reaction chamber under high pressure and pulsed, allowing some of the enzymes to bind. Again, the unbound enzyme is pumped out before sequencing begins. In one embodiment of the invention, the use of low temperature and non-optimal pH is contemplated to help ensure that the enzyme does not step by more than one base during the binding pulse.

Alternative embodiments of the sequencing instrument are contemplated. In one embodiment, decreasing the volume of the reaction chamber and of the flow path to the detector significantly reduces the time interval between pulses. In another embodiment, the immobilized DNA is suspended in a flow stream using the techniques proposed for single molecule sequencing (Jett, J. H. Keller, R. A., Martin, J. C., Marrone, B. L., Moyzis, R. K. Ratliff, R. L. Seitzinger, N. R., Shera, E. B. and Stewart, C. C., (1989) "High-Speed DNA Sequencing: An Approach Based Upon Fluorescence Detection Of Single Molecules," *J. Biomol. Struct. Dyn,* 7:301–309). In still another embodiment, the detection speed is increased by using multiple detectors and rapidly diverting the flow stream from the reaction chamber from one detector to the next. When these improvements are combined, it is contemplated to use a single pressure pulse to initialize the exonuclease on substrates. The unbound enzymes would be washed out. A decrease in pressure would then allow the enzymes to hydrolyze the DNA at normal-speed. Since the enzymes are all starting at the same point and are all utilizing identical substrates, they may stay synchronized for a relatively long time period. The rate of hydrolysis by exonuclease I from *E. coli* has been reported to be 275 bases/second (Brody, R. S., Doherty, K. G. and Zimmerman, P. D., (1986) "Processivity and kinetics of the reaction of exonuclease I from *E. coli* with polydeoxyribonucleotides," *J. Biol. Chem.,* 261:7136–7143). At a rate of 200 bases/second a 10,000 base length of DNA could be sequenced in less than a minute.

H. Evaluation of Enzymes

In general, processive enzymes that repeatedly catalyze chemical reactions while remaining bound to and moving along a particular substrate are preferred. The procedures by which candidate polymerases and exonucleases are screened for use with the methods of controlling enzyme activity are set forth below and summarized in Table 1.

The temporal steps involved in the screening process are as follows:

I. Add enzyme to substrate solution, apply pressure until enzyme in inactive (i.e., inhibitor pressure), then reduce pressure to determine if enzyme has retained activity (i.e. permissive pressure).

II. For an enzyme that has retained activity, determine the ranges of pressures (by repeating procedure of Step I) under which enzyme can be reversibly inhibited and under which enzyme exhibits acceptable activity.

III. Determine the range of temperatures under which enzyme can remain reversibly active.

IV. Determine the optimum conditions of temperature and pressure for maintaining synchronous processing of the substrate by enzyme.

TABLE 1

| Step | Determination | Conclusion |
| --- | --- | --- |
| I | Enzyme Irreversibly Inhibited | Enzyme Not Viable Candidate |
| I | Enzyme Activity Retained | Proceed To Step II |
| II | Pressure Ranges | Proceed To Step III |
| III | Temperature Ranges | Proceed To Step IV |
| IV | Optimum Conditions (Temp./Press.) | Practice Invention With Enzyme |

As illustrated below, thoughtful consideration of the procedures set forth above allows any enzyme ("X") can be evaluated for use with the present invention.

An enzyme ("X") can be evaluated for use with the contemplated method of pressure control (i.e., using a synchronized enzyme activity to treat a substrate such as nucleic acid). Enzyme X is initially evaluated according to Step I by adding X to the substrate solution under appropriate conditions (e.g., cold temperature). Thereafter, pressure is applied until X is rendered inactive, then reduced to achieve a pressure under which X normally would be active; this allows a determination of whether X has retained activity. Some enzymes may require a recovery period at low pressure before they regain activity after high pressure treatment. If X does not regain activity, then X has denatured due to irreversible changes in its secondary and tertiary structure. However, it is important to remember that an enzyme capable of reversible inhibition may be raised to a pressure that is too high, thus causing irreversible inhibition. Therefore, when an enzyme has not regained activity, one must be certain that a lower pressure would not successfully cause the enzyme to be reversibly inhibited.

After enzyme X has demonstrated reversible inhibition, the range of pressures under which X can be reversibly inhibited and under which X exhibits acceptable levels of activity is evaluated (Step II). Step II can be readily accomplished by progressively repeating Step I until the desired ranges are 10 ascertained. That is, the range of inactivation pressures (e.g. between 20,000 and 50,000 psi) can be readily determined by progressively raising the inactivation pressure of Step I until irreversible inhibition is achieved (some enzymes maybe stable at the pressure limits of the same equipment) and progressively lowering the inactivation pressure of Step I until X is no longer inhibited. The range of pressures under which X exhibits acceptable levels of activity can be ascertained by undertaking a similar series of steps. The range of inactivation pressures denotes those pressures that must be achieved to reversibly inhibit the enzyme during each pressure pulse, while the range of activation pressures denotes those pressures that must be reached to allow controlled processing of the substrate by the enzyme.

Next Step III entails a determination of the range of temperatures under which enzyme X can remain reversibly active while simultaneously being subjected to the pressures previously determined in Step II. Step III can be accomplished in a manner analogous to that described in Step II. That is, the range of temperatures (e.g. 5 to 60° C.) is determined by progressively raising the temperature until X is irreversibly inactivated and then lowering the temperature in a similar fashion.

The final step, Step IV, involves determination of the optimum conditions of temperature and pressure for maintaining synchronous processing of the substrate by X. It should be noted that several different temperatures might be determined in Step IV. For example, a low temperature (e.g. 5–10° C.) can ensure that X does not step by more than one nucleotide base during the binding pulse of pressure. Similarly, various ratios of temperature-to-pressure can assist in,finely controlling the rate of X's activity.

The following examples illustrate certain embodiments and aspects of the present invention and are not to be construed as limiting the scope thereof.

EXAMPLES

In the experimental disclosure which follows, the following abbreviations apply: °C. (Centigrade); MPa (megaPascal); psi (pounds per square inch); $\mu$g (micrograms); $\mu$l (microliters); ml (milliliters); and mM (milliMolar). Units of pressure can be converted as follows: 1 atmosphere=101.3 kPa=14.5 psi.

Example 1

Lambda Exonuclease

In this example, the control over the activity of lambda exonuclease is demonstrated using hydrostatic pressure. For these experiments the following assay buffer was used: 67 mM glycine-KOH (pH 9.4), 2.5 mM $MgCl_2$ and 50 $\mu$g/ml acetylated BSA. The substrate used in these experiments was a Hind III digest of lambda DNA. Digestion of lambda DNA with Hind III yields eight fragments that range in size from 125 up to 23,130 base pairs. The assay components were mixed at the following ratios: 1.0 $\mu$l of 10×assay buffer+2.0 $\mu$l of Hind III digested lambda DNA (0.24 $\mu$g/$\mu$l)+0.5 $\mu$l of acetylated BSA (1.0 $\mu$g/$\mu$l)+1.0 $\mu$ exonuclease (at the desired concentration)+5.5 $\mu$l of $H_2O$. The stock lambda exonuclease solution (2.0 units/$\mu$l from Life Technologies) was diluted in assay buffer to the desired concentration. For a typical high pressure experiment the above components were mixed at the specific ratios to yield a final volume of 40 $\mu$l. The cold (0–50° C.) reagents were mixed at ambient pressure and the enzyme was added last to initiate the reaction. Next 10 $\mu$l of the solution was removed and placed in a 1.5 ml microfuge tube. This was used as the dead time control. The remainder of the assay mix was loaded into a small polyethylene capsule prepared by drawing out the end of a disposable transfer pipette. The capsule is sealed by folding over the reduced ends which are held in place by crimping a small aluminum band over the folded ends. The capsule is then placed in the reaction chamber of a manually operated pressure apparatus where the pressure is quickly elevated to desired level. The sum of the time it takes to load a capsule and get it under pressure, plus the time it takes to release the pressure and recover the sample from the capsule, is referred to as the dead time. The dead time was 8 to 10 minutes. The dead time controls are used to determine the extent of the reaction that take place while not under pressure. All reactions are stopped by the addition of 4 $\mu\mu$l of gel loading buffer (250 mM EDTA, 0.25% xylene cyanol, 0.25% bromophenol blue and 30% glycerol). The sample is incubated at the selected pressure for the desired period of time. The pressure is then release and a 10 $\mu$l aliquot of the recovered assay mixture is stopped by adding it to 4 $\mu$l of gel loading buffer. The remainder of the recovered sample can be incubated at ambient pressure for 15 minutes to determine the recovery of enzyme activity after pressurization.

The enzyme reaction was followed by separating the DNA fragments on a 0.5% agarose gel in TBE buffer. The DNA bands were stained with ethidium bromide and photographed on a transilluminator. The enzyme activity causes a decrease in the substrate bands as they are converted into smaller single stranded product which stain poorly.

Figure 13:
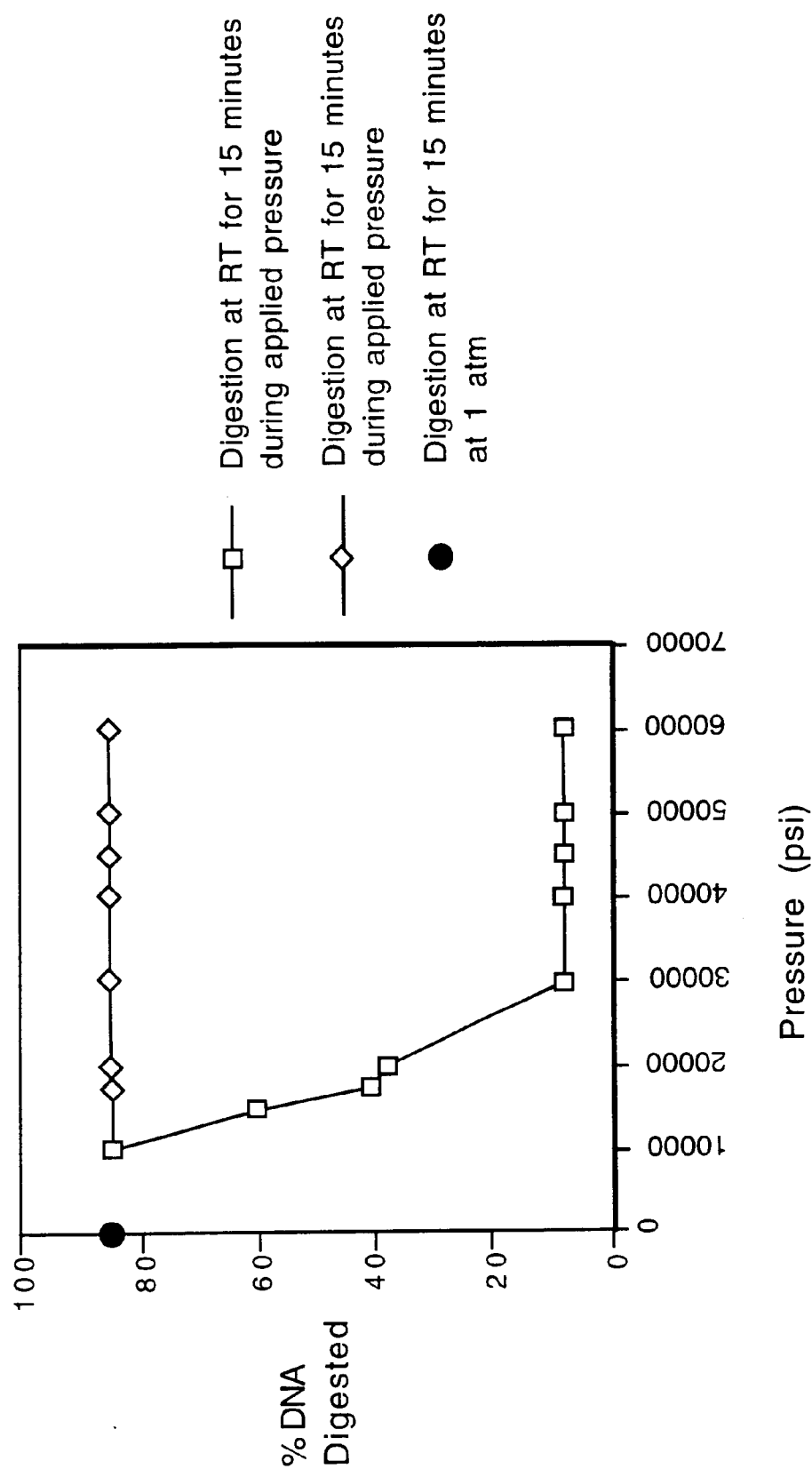
FIG. 13 is a graph showing the effect of applied hydrostatic pressure on the digestion of DNA by lambda exonuclease.

The results (FIG. 13) demonstrated that Lambda exonuclease activity is affected very little by a pressure of 10,000 psi at a temperature of 20–21° C. Inhibition of enzyme activity is evident at 15,000 psi. Inhibition of enzyme activity is increased further at 17,500 psi and 20,000 psi. Enzyme activity appears to be completely inhibited at 30,000 psi. When the reaction mixture is held at an inhibitory pressure for one hour, then rapidly returned to ambient pressure for 15 minutes, the enzyme activity appears to be fully recovered. The enzyme is very stable to high pressures. A 15 minute incubation in the presence of substrate at 60,000 psi did not effect the recovered activity. These results demonstrate that lambda exonuclease can be reversibly inhibited by high hydrostatic pressure. One cycling experiment, in which the pressure was cycled between 30,000 and 250 psi for 43 cycles at an average time below 30,000 psi of 17.7 seconds, was performed. The resulting substrate banding pattern, after agarose gell electrophoresis, was that of a processive enzyme.

Therefore, a pressure of 30,000 psi did not causing the enzyme to dissociate from the substrate.

Example 2

T4 DNA Polymerase

In this example; the double-stranded 3'–5' exonuclease activity of T4 DNA polymerase was measured by using DNA size markers as substrates, separating the size markers by agarose gel electrophoresis, and visualizing the markers with ethidium bromide detection (Sambrook, J., Fritsch, E. F. and T. Maniatis, (1989) *Molecular Cloning: A Laboratory Manual,* 2nd ed., p. 6.3–6.19). Exonuclease activity will cause the bands to shift to lower sizes on the gel.

The 3' to 5' exonculease activity of. T4 DNA polymerase (United States Biochemical) was evaluated under pressure at room temperature in the enzyme buffer supplied by the manufacturer and in a manner essentially as described in Example 1. At atmospheric pressure approximately 100 base pairs were digested in 20 minutes, as evidenced by band shifts on a 0.5% agarose gel. In the absence of substrate, the enzyme was completely and irreversibly inactivated by a one hour incubation at pressures of 30,000 psi and greater.

In the presence of substrate a pressure of 40,000 psi was required to completely and irreversibly inactivate the enzyme during a one hour incubation. A one hour incubation, in the presence of substrate, at 30,000 psi resulted in the deletion of approximately 100 base pairs from the lambda DNA, as indicated by band shifts on a 0.5% agarose gel. These data demonstrate that the activity of the enzyme can be irreversibly terminated by applying the appropriate pressure to the capsule, thereby providing a means for precision control of the extent of the digestion of the DNA.

Example 3

Controlled Digestion By Lambda Exonuclease

In this example, hydrostatic pressure is used to control the extent of digestion by lambda exonclease. The DNA substrate for these experiments was plasmid pBR322 digested with Eco R V to give the linear form. A 10 $\mu$l assay volume was used in these experiments. For these experiments, a 5 $\mu$l substrate mix and a 5 $\mu$l enzyme mix were prepared and chilled on ice. The substrate mix contained 4 $\mu$l of 1.33× assay buffer+1 $\mu$l of linear pBR322 DNA (approx. 0.25 $\mu$g). The enzyme mix contained 4 $\mu$l of 1.33×assay buffer+1 $\mu$l of lambda exonuclease (3.3 units). The 1.33×assay buffer contained 10 $\mu$l of 10×lambda exonuclease buffer +4 $\mu$l of acetylated BSA (1.0 $\mu$g/$\mu$l)+61 $\mu$l of distilled water [10× lambda exonculease buffer contained the following: 670 mM glycine-KOH (pH 9.4) and 25 mM MgCl$_2$]. To start an experiment the enzyme mix was added to the substrate mix on ice. This solution was then loaded into a capsule as described above (See p. 18). The capsule-was then placed in a 50° C. reaction chamber and the pressure was quickly raised to 50,000 psi. The valve to the reaction chamber was closed and the reaction chamber, still under pressure, along with the valve were disconnected from the apparatus and placed in a 20° C. water bath for 30 minutes.

The valve and reaction chamber were then reconnected to the apparatus and the pressure was quickly reduced to 10,000 psi and held there for the desired time period. The pressure was then increased to 30,000 psi. The valve and reaction chamber were then disconnected from the apparatus and placed in a −70° C. freezer. The frozen sample was then recovered as above (See p. 18).

The substrate DNA was analyzed by agarose gel electrophoresis as above. The higher concentration of enzyme used in these experiments causes the substrate band to shift to a smaller size as the enzyme digestion proceeds.

The results demonstrated that the extent of digestion by lambda exonuclease can be controlled by limiting the time spent at the permissive pressure. A comparison between the dead time lane and the experimental lanes demonstrates that as the length of time spent at 10,000 psi increases, so does the extent of digestion.

Example 4

Effect of Pressure on the Rate of Digestion by Lambda Exonuclease

In this example the rate of digestion (i.e., the number of bases removed per second) by lambda exonuclease was determined at various pressures and two temperatures. The substrate used in this example was a Hind III digest of lambda DNA. In these experiments the reaction chamber pressure was set during the initial pressurization and remained constant throughout the experiment, and the reaction chamber remained in the water bath during the entire time period of the experiment. With the exceptions noted above, the experiment were carried out as described in Example 3.

The rate at which nucleotide monophosphates were being removed from the ends of the substrate bands was determined by estimating the size in base pairs of the shifted bands seen after agarose gel electrophoresis. Standard curves were constructed by plotting the migration distance versus Log [base pairs] of Hind III fragments not treated with enzyme.

Figure 14:
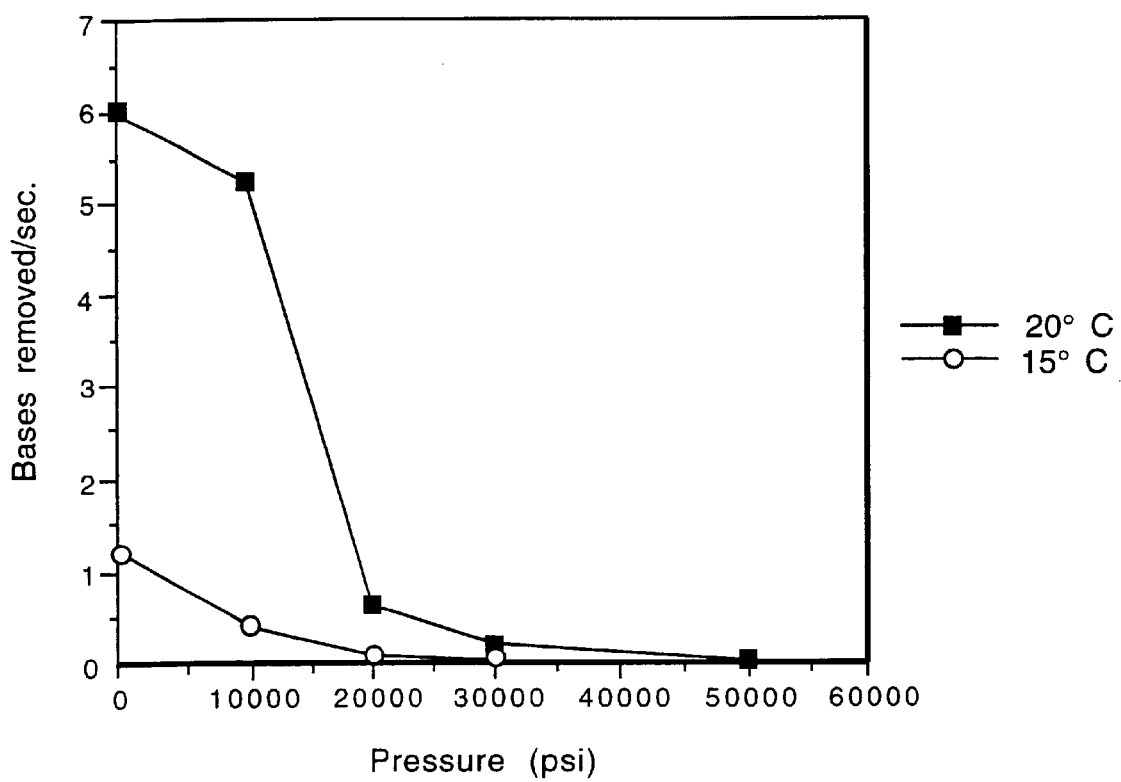
FIG. 14 is a graph showing the effect of various applied hydrostatic pressures and temperatures on the digestion of DNA by lambda exonuclease.

At a temperature of 20° C. pressures of 10,000 psi and below had little effect on the rate of lambda exonuclease. Pressures of 20,000 psi and above significantly decrease the rate. At a temperature of 15° C., pressures greater than or equal to 10,000 psi cause significant decreases in the rate. The data (FIG. 14) indicated that, while it appeared from earlier experiments the enzyme was completely inhibited at 30,000 psi, this is not the case. The apparent inhibition was due to the less sensitive assay employed.

Example 5

Comparison of Five Pressure Cycles to One Pressure Cycle of Equal Duration at the Permissive Pressure In this example the band shifts produced by five two-minute cycles of pressure are compared to those of a single ten-minute cycle. In both cases 50,000 psi was used as the inhibitor pressure and 5,000 psi was used as the permissive pressure. The experiments were performed as described in Example 3, with the following exceptions: the substrate mix contained 0.34 $\mu$g of Hind III digested DNA. The enzyme mix contained 0.8 units of lambda exonuclease. The pressure cycle was as described above and the freeze stop was carried out at 50,000 psi.

The results, shown in FIG. 6, demonstrate that both cycling protocols give the same pattern of bands, thus indicating that the four additional starts and stops in the five-cycle experiment did not produce a detectable effect on the extent of digestion. The results also suggest that the enzyme is not dissociating at 50,000 psi based on the fact that original-length substrate bands are also seen on the gel.

From the above, it should be clear that the present invention provides an improved method for controlling enzyme activity on substrates. In the case of nucleic acid, the invention allows for treatment of nucleic acid and the generation of nested deletions wherein the extent of digestion can be controlled. The ability to control the extent of digestion will allow the routine generation of groups of deletions having widely or tightly clustered lengths, depending on the ultimate use for the nested deletion mutants.

Example 6

Sequenase 2.0

The activity of Sequenase 2.0, the synthetic form of processive enzyme T7 DNA polymerase (E.C. 2.7.7.7) (U.S. Biochemical Corp., Cleveland, Ohio) was assayed using Lambda Hind III fragments as substrate.

The Lambda fragments were partially digested in the 3' to 5' direction by the 3' to 5' exonuclease activity of T4 DNA polymerase (New England Biolabs, Beverly, Mass.). The following were combined in a 0.65 ml microcentrifuge tube: 5×Sequenase buffer (12 $\mu$l), lambda Hind III (0.34 $\mu$g/$\mu$l), and 36 $\mu$l water. 5×Sequenase buffer contains 200 mM Tris-HCl, pH 7.5, 100 mM MgCl$_2$, and 250 mM NaCl. The tube was placed in a 65° C. water bath for 3 minutes, followed by an ice bath. After adding 6 µl of T4 DNA polymerase (3 units/µl) to the tube, the tube was then incubated in a 37° C. bath for 1 hour. After chilling the tube on ice for 2–5 minutes, the contents of the tube were transferred to a capsule, and the capsule was loaded into the chilled reaction chamber of version 1. The capsule was custom-made by heat sealing one end of a polyethylene transfer pipet and cutting to length. The reaction chamber pressure was raised to 50,000 psi and maintained for 1 hour to inhibit the T4 DNA polymerase. After returning the chamber pressure to atmospheric pressure over 2–4 minutes, the substrate mixture was removed from the capsule.

The above substrate solution was made to 5.9 mM in DTT by the addition of 2 µl of 100 mM DTT per 32 µl of solution. Eight and one-half microliters of this diluted solution was placed in a capsule and 1 µl of diluted Sequenase (3 units/µl) was added. The capsule was then placed in the open chilled (−5° C.) reaction chamber of version 2 and incubated for 2 minutes to cool the capsule. After pipetting 1 µl of cold (approx. 0° C.) dNTP solution into the capsule in the open reaction chamber, the solution in the capsule was overlaid with about 20 µl cold silicone oil (melting point bath oil, Sigma Chemical Co., St. Louis, Mo.). The dNTP solution contained: 4 mM dATP, 4 mM dCTP, 4 mM dGTP, 4 mM dTTP, 40 mM Tris-HCl, pH 7.5, 20 mM MgCl$_2$ and 50 mM NaCl. The reaction chamber was then sealed and pressurized to the desired pressure.

A 20±1° C. thermostated solution was circulated around the reaction chamber to raise the temperature of the reaction chamber and capsule to the operating temperature. A standard 10 minute incubation at the selected test pressure was run to allow the capsule temperature to reach the operating temperature. Three different pressure profiles (1)–(3) were followed to determine the response of the enzyme activity to pressure. In these experiments, the transition times were longer than necessary because temperature was used. (1) At every pressure (20,000, 30,000 and 40,000 psi) a dead time experiment was run. This experiment determined whether there was any enzyme activity during the loading and recovery of the sample. Profile: 40,000 psi, thermostated solution 20° C., 10 minutes (see above); 40,000 psi, thermostated solution −12±2° C., 12 minutes; drop pressure to atmospheric pressure and recover frozen sample.

(2) To determine enzyme activity at pressure, the following profile was used: 40,000 psi, thermostated solution 20° C., 10 minutes (transition time from atmospheric to 40,000 psi was between 5 and 15 seconds); 40,000 psi, thermostated solution 20° C., 20 additional minutes; 40,000 psi, thermostated solution −12±2° C., 12 minutes; drop pressure to atmospheric pressure (transition time was between 5–15 seconds) and recover frozen sample.

(3) To determine enzyme activity after pressure treatment, the following profile was used: 40,000 psi, thermostated solution 20° C., 10 minutes; 40,000 psi, thermostated solution 20° C., additional 20 minutes; drop pressure to 300±150 psi in a transition time of 25 msec. thermostated solution 20° C., 10 minutes; drop pressure to atmospheric pressure, thermostated solution 20° C., and recover sample.

Each sample was recovered from the capsule by cutting off the sealed end of the capsule and centrifuging the contents of the capsule with 4 µl of 50 mM EDTA pH 8.0, 0.35% sodium dodecyl sulfate, 17.5% glycerol. The size of the DNA fragments in the sample was determined by electrophoresis on a 0.5% agarose gel. As in Example 8 below, in this assay Sequenase activity caused the diffuse small sized substrate bands to shift to larger sized bands of defined size. After electrophoresis the DNA bands were detected by staining with ethidium bromide and the gel was photographed. Sequenase activity was estimated by visual inspection of the photograph (see Table 2, results are ∓10%). A band pattern of the enzyme under pressure which appeared identical to the dead time band pattern was interpreted as indicating no detectable enzyme activity at that pressure. The presence of bands with defined sizes in the post pressure sample (3) were interpreted as indicating recovery of enzyme activity after pressure treatment.

TABLE 2

| Pressure Activity | Activity | Post-Pressure |
|---|---|---|
| 20,000 | some | not determined |
| 30,000 | none | full activity |
| 40,000 | none | 25% of orig. activity |

EXAMPLE 7

Restriction Endonuclease Hind III

The activity of restriction endonuclease Hind III (E.C. 3.1.21.4), a distributive enzyme, was assayed at 37° C. using as a substrate a biotinylated PCR product having two Hind III cleavage sites.

The PCR product was generated using a biotinylated Lac Z forward primer and a Lac Z reverse primer (Genosys Biotechnologies Inc., Woodlands, Tex.). The dCTP was from Promega, Madison, Wis. The control template and all other components for the PCR reaction were from a PCR Nonradioactive Labeling system from Life Technologies, Gaithersburg, Md. The PCR product from this system is a 898 base pair fragment that contains to Hind III cleavage sites. One approximately 126 base pairs from the biotinylated end and another approximately 348 base pairs from the biotinylated end. DNA mix contained 0.5 µl PCR product (approx. 25 ng), 0.5 µl 10×buffer, and 4 µl water. Enzyme mix contained 1 µl Hind III (100 units/µl, New England Biolabs, Beverly, Mass.), 0.5 µl 10× buffer, and 3.5 µl water. 10×buffer contained 100 mM Tris-HCl, pH 7.9, 100 mM MgCl$_2$, 500 mM NaCl, and 10 mM DTT.

The above DNA and enzyme mixes were chilled on ice in separate tubes. Five microliters of enzyme was added to 5 µl of DNA solution, mixed on ice, quickly transferred to a chilled capsule and overlaid with cold (about −15° C.) silicone oil. After loading the capsule into a chilled (−5° C.) reaction chamber (version 2), the reaction chamber was pressurized to 30,000 psi. The pressure was maintained at 30,000 psi with a thermostated 37° C. solution circulating around the reaction chamber for 10 minutes. A single pressure pulse of 4 seconds was applied. The pulse changed the pressure to 300 psi ∓200 psi while the reaction chamber was thermostated at 37° C. The transition time was approximately 25 milliseconds. While maintaining the pressure at 30,000 psi, a −12° C. thermostated solution was circulated around the reaction chamber for 12 minutes to ensure enzymatic inhibition in the next step, wherein the pressure was lowered to atmospheric pressure, and the chilled capsule was removed.

Additional samples were run as above except the single cycle times were 8, 12, 16 and 20 seconds. A dead time without a negative pressure was also run. The samples were recovered as in example 6. The samples were analyzed by electrophoresis on a 2% agarose gel and stained with ethidium bromide. The dead time sample had no product gel bands, i.e., there was no detectable activity at 30,000 psi. The 4-second pulse sample had faint product bands and the intensity of the product bands increased as the pulse time increased from 4 to 20 seconds. The 20-second pulse sample had a faint substrate band indicating that the digestion was not complete after 20 seconds of enzymatic activity.

Enzymatic activity was inhibited at 30,000 psi ($\mp 6\%$). Reducing pressure to 300 psi $\mp 200$ psi ambient pressure restored the enzymatic activity.

Example 8

Lambda Exonuclease with Multiple Short Pressure Pulses

In this experiment lambda exonuclease digestion of lambda Hind III fragments was studied using many short pressure pulses. The DNA mix per assay contained: 2 $\mu$l lambda Hind III fragments (0.34 $\mu$g/$\mu$l, IBI, New Haven, Conn.) and 8 $\mu$l of 1.33×assay buffer. The enzyme mix contained per assay: 1 $\mu$l lambda exonuclease (5 units/$\mu$l, Life Technologies Inc., Gaithersburg, Md.), 1 $\mu$l water and 8 $\mu$l 1.33×assay buffer. [1.33×assay buffer contained: 89 mM glycine-KOH, pH 9.4, 3.3 mM MgCl$_2$, BSA 34 $\mu$g/ml] the above DNA and enzyme mixes were chilled on ice in separate tubes. Then the 10 $\mu$l of enzyme was added to the 10 $\mu$l of DNA solution and mixed on ice. This mixture was then immediately transferred to a chilled capsule (approx. −15 to −5° C.) in a cold block (approx. −20 to −10° C.) and overlaid with cold (approx. −20 to −15° C.) silicone oil. The capsule was then loaded into the chilled (−5° C.) reaction chamber of version 2 and pressurized. The pressure was then held at 30,000±2,000 psi, and a thermostated 20° C. solution was circulated around the reaction chamber for 12 min. The pressure in the reaction chamber was then pulsed to 300±100 psi for 210±20 mseconds with a cycle time of 2.02±0.02 seconds. The pulse time is an estimate according to oscilloscope measurements of the total time below 30,000 psi and is equal to $\delta t_{a,y}+t_{a,y}+\delta t_{i,z}$. The oscilloscope only measured the total time below 15,000 psi which was 170±20 mseconds. The time from one pulse to the next including the pulse time was 2.02 seconds). The reaction chamber and sample were pulsed for a total of 594±2 times. With the pressure at 30,000 psi, a −12° C. thermostated solution was circulated around the reaction chamber for 12 min. to freeze the sample in the capsule. The pressure was then dropped to atmospheric pressure in about 30 mseconds. The sample was recovered as in Example 6, except that 8 $\mu$l of stop buffer was used. A dead time plus 17 min. at 30,000 psi sample without pulsing was also run. The above samples were run on a 0.5% agarose gel containing 1.3 $\mu$g/ml ethidium bromide and 0.5×TBE=(45 mM Tris-borate, 1 mM EDTA). The gel was run at 23 volts for 16 hours and then photographed. The dead time plus 17 min. sample was used to estimate the enzyme activity that had occurred at 30,000 psi during the pulsing experiment. At 30,000 psi and 20° C., the enzyme has a rate of about 0.1 bases/second. The band shifts in the pulsed sample were larger than in the dead time plus 17 min. sample. The total number of bases removed in the pulsed sample minus the number of bases removed in the dead time plus 17 minute sample yields the number of bases removed during the pulses. The average number of bases removed during the pulsing was 350±60; thus, the enzyme was hydrolyzing an average of 0.6 bases per pulse.

Example 9

Lambda Exonuclease with Multiple Short Pressure Pulses with Different Pulse Lengths In this experiment lambda exonuclease action on lambda Hind III fragments was studied at various pressure pulse lengths. The DNA mix per assay contained: 2 $\mu$l Lambda Hind III fragments (0.34 $\mu$g/$\mu$l, IBI) and 8 $\mu$l of 1.33×assay buffer. The enzyme mix contained per assay: 1 $\mu$l lambda exonuclease (5 units/$\mu$l, Life Technologies Inc., Gaithersburg, Md.), 1 $\mu$l water and 8 $\mu$l 1.33×assay buffer. 1.33×assay buffer contained: 89 mM glycine-KOH, pH 9.4, 3.3 mM MgCl$_2$, and BSA 34 $\mu$g/ml. The above DNA and enzyme mixes were chilled on ice in separate tubes. Then the 10 $\mu$l of enzyme was added to the 10 $\mu$l of DNA solution and mixed on ice. This mixture was then immediately transferred to a chilled capsule (approx. −15 to −5° C.) in a cold block (approx. −20 to −10° C.) and overlaid with cold (approx. −20 to −15° C.) silicone oil. The capsule was then loaded into the chilled (−5° C.) reaction chamber of version 2.0 and pressurized. The pressure was then held at 40,000±2,000 psi, and a thermostated 20° C. solution was circulated around the reaction chamber for 8 min. The pressure in the reaction chamber was then pulsed to 300±100 psi for 430±20 mseconds with a cycle time of 2.02±0.02 seconds. The pulse time is an estimate of the total time below 40,000 psi and is equal to $\delta t_{a,y}$ (transition time from 40,000 psi to 300 psi)+$t_{a,y}$ (time at 300 psi)+$\delta t_{i,z}$ (transition time from 300 psi to 40,000 psi). The cycle time equals the pulse time plus the time at 40,000 psi after $\delta t_{i,z}$ but before $\delta t_{a,y}$. According to the oscilloscope, the pulse time below 20,000 psi was 370±20 msec. The time from one pulse to the next including the pulse time was 2.02 seconds. The reaction chamber and sample were pulsed for a total of 500±2 times. With the pressure at 40,000 psi a −12° C. thermostated solution was circulated around the reaction chamber for 12 min. to freeze the sample in the capsule. The pressure was then dropped to atmospheric pressure in about 15 milliseconds. The sample was recovered as in example 6 except that 8 $\mu$l of stop buffer was used. An additional sample was run as above using a pulse time of 590±20 milliseconds. A control sample subjected to dead time plus 12 min. 23 seconds at 40,000 psi without pulsing was also run. The above samples were run on a 0.5% agarose gel as described in Example 7. The dead time plus 12 min. 23 sec. sample showed no detectable activity; the bands were similar to the bands resulting from no enzyme control. For the pulsed samples, the leading edge of a shifted band was used to determine the number of bases digested by the exonuclease. With a pulse time of 430 msec. the enzyme was hydrolyzing an average of 0.6±0.2 bases per pulse and at a pulse time of 590 msec. the enzyme was hydrolyzing an average of 1.1±0.2 bases per pulse.

Example 10

Version 3.0 Flow-through with Rapid Pulse

A PCR product is generated using a target DNA of known sequence, one 5'-NH$_2$ primer and one 5'-phosphate primer. This PCR product is immobilized on an amine reactive solid support (e.g. EMPRAZE™ beads, 3M, St. Paul, Minn.). The immobilization of the PCR product limits the digestion by lambda exonuclease to only the free 5'-end (i.e. the phosphorylated end). The solid support with the immobilized DNA is placed in the reaction chamber and loaded into version 3.0. The reaction chamber is fitted with two frits of sufficient pore size to retain the beads and contains a sufficient volume of beads to permit subsequent detection of reaction products.

The reaction chamber is washed with buffer A (67 mM glycine-KOH, pH 9.4) at atmospheric pressure. The reaction chamber and wash solutions flowing into it are equilibrated to a temperature of 20° C. The reaction chamber is then washed with buffer A which also contains 50 $\mu$g/ml BSA and 5 units/20 µl of lambda exonuclease. In the absence of $Mg^{++}$ the enzyme binds to DNA but is not catalytically active. The pressure in the reaction chamber is raised to 40,000 psi, and the chamber is then washed with buffer A containing 2.5 mM $MgCl_2$ (buffer B). The pressure in the chamber is then pulsed to 300±200 psi for 590 mseconds. The pressure is returned to 40,000 psi at the end of the pulse. The chamber is then washed at 40,000 psi with 100–300 µl of buffer B to remove the free nucleotide 5'-monophosphate released by the action of lambda exonuclease. The wash is collected for later analysis. Subsequent 590 msecond pulses and washes are repeatedly applied as above. The washes are collected for analysis.

The collected washes are analyzed by mass spectrometry to identify the nucleotide 5'-monophosphates present in each wash. This information is used to determine the nucleotide sequence of the strand digested by lambda exonuclease.

OTHER EMBODIMENTS

From the description above, one skilled in the art can ascertain the essential characteristics of the invention and without departing from the spirit and scope thereof, can make various changes and modifications of the invention to adapt it to various usages and conditions. All references cited herein are incorporated by reference.

For example, the disclosed reactor can also be used in Processes such pasteurization, sterilization, inactivation of protein toxins, meat tenderization, solubilization of gas in a liquid, degassing liquids, dewatering or extraction, alteration of metabolism and gene expression of microorganisms, study of barophilic microorganisms, crystallization and purification of materials, and industrial treatment of surfaces such as impregnation of coatings.

What is claimed is:

1. A pressure cycling reactor for conducting a controlled pressure sensitive reaction comprising,
    a reaction vessel for containing a sample,
    a vessel pressurizer connected to the reaction vessel, and
    a controller connected to the vessel pressurizer for signalling the pressurizer to maintain reaction inactivating pressure $P_1$ in the reaction vessel and signalling the pressurizer to change pressure in the reaction vessel to a reaction activating pressure $P_2$ for a pulsed period $t_1$ and then recycling to a reaction inactivating pressure $P_3$ in the reaction vessel.

2. The pressure cycling reactor of claim 1 wherein said pressurizer is capable of achieving a change in pressure of over 20,000 psi in less than 250 milliseconds.

3. The pressure cycling reactor of claim 1 further including a fluid source in communication with said reaction vessel.

4. The pressure cycling reactor of claim 1 wherein said vessel pressurizer includes a pressure chamber, said pressure chamber being connected to said reaction vessel such that said pressure chamber communicates with said reaction vessel responsive to said controller.

5. The pressure cycling reactor of claim 4 wherein said pressure chamber comprises a pneumatic pump cylinder.

6. The pressure cycling reactor of claim 4 wherein said pressure chamber has a variable volume, said pressurizer further including a pressure transmitter for connection to a pressure source, said pressure transmitter being connected to a pressure chamber wall to control the position of the wall and thereby control the pressure chamber volume.

7. The pressure cycling reactor of claim 6 wherein said pressure transmitter comprises a pneumatic cylinder.

8. The pressure cycling reactor of claim 6 further including a relief valve for adjusting the pressure in said pressure transmitter thereby creating a pressure pulse in said reaction vessel.

9. The pressure cycling reactor of claim 4 further including a pressure chamber outlet valve positioned between said pressure chamber and said reaction vessel.

10. The pressure cycling reactor of claim 4 further including a fluid source in communication with said reaction vessel, and a pressure chamber inlet valve positioned between said fluid source and said pressure chamber.

11. The pressure cycling reactor of claim 10 wherein said fluid source comprises a fluid reservoir connected to a reservoir pressure source, and a reservoir control valve, whereby fluids are moved from said fluid reservoir to said reaction vessel via said pressure chamber, while pressure in said reaction vessel is controlled.

12. The pressure cycling reactor of claim 11, further comprising a temperature sensor connected to said fluid reservoir and a reservoir vessel heating and/or cooling source, whereby the temperature of the fluid in the reservoir is controlled.

13. The pressure cycling reactor of claim 1 further including a pressure sensor connected to said reaction vessel and to said controller, whereby the controller monitors the pressure in said reaction vessel.

14. The pressure cycling reactor of claim 13 further including a pressure regulator for adjusting the pressure in said pressure chamber, said controller using feedback from said pressure sensor to control said pressure regulator.

15. The pressure cycling reactor of claim 1, wherein said vessel pressurizer is a first vessel pressurizer, said reactor further comprising a second vessel pressurizer connected to the reaction vessel, whereby fluids are removed from said reaction vessel while pressure in said reaction vessel is controlled.

16. The pressure cycling reactor of claim 15 further including a second vessel pressurizer inlet valve located between said reaction vessel and said second vessel pressurizer.

17. The pressure cycling reactor of claim 15 further including a second fluid reservoir and a second vessel pressurizer outlet valve located between said second fluid reservoir and said second vessel pressurizer.

18. The pressure cycling reactor of claim 17 further including a second reservoir control valve connected to said second fluid reservoir.

19. The pressure cycling reactor of claim 15 wherein said controller controls a plurality of valves according to a predetermined set of stored signals which control the valves to add at least one pressurized reagent fluid to the reaction vessel and to remove at least one pressurized reacted fluid from the reaction vessel, while the reaction vessel remains under pressure.

20. The pressure cycling reactor of claim 1, further comprising a temperature sensor connected to said reaction vessel and a reaction vessel heating and/or cooling source, whereby the temperature of the reaction vessel is controlled.

21. The pressure cycling reaction of claim 1, further comprising a detector connected to the reaction vessel in a manner that allows it to detect a characteristic of a component present in a sample in or removed from the reaction vessel.

22. The pressure cycling reactor of claim 21 in which the detector is selected from the group consisting of a radioisotopic detector, an infra-red spectrometer, a mass spectrometer, a gas chromatography-mass spectrometer, a spectrophotometer, a spectrofluorometer, an electrochemical detector, a surface plasmon resonance detector, and a photometer.

23. The pressure cycling reactor of claim 1 wherein said reaction vessel includes a restraint to retain an immobilized reagent within the reaction vessel while permitting removal of fluid from the vessel.

24. The pressure cycling reactor of claim 23 wherein said immobilized reagent comprises an organic compound attached to a non-liquid support.

25. The pressure cycling reactor of claim 23 wherein said restraint comprises a semi-permeable barrier which divides the reaction vessel into two segments.

26. A reactor for intermittently inhibiting activity of a sample by controlling temperature and pressure conditions of the sample, comprising:
- a reactor body defining a chamber for receiving the sample,
- a pressurizer in communication with said chamber mounted for movement between a first position for applying a first predetermined pressure $P_1$ to said chamber, said first predetermined pressure $P_1$ being selected to inhibit activity of the sample, and a second position for changing said chamber pressure to a second predetermined pressure $P_2$ selected to allow activity of the sample,
- a switch having a first state and a second state to move said pressurizer between said first position and said second position,
- a controller for changing said switch between said first and second states,
- means for adjusting temperature in said chamber, and
- a port in communication with said chamber for removal of the sample from said chamber.

27. The pressure cycling reactor of claim 1 wherein said vessel pressurizer is a first vessel pressurizer, said reactor further comprising a second vessel pressurizer connected to the reaction vessel, whereby fluids are introduced into said reaction vessel while pressure in said reaction vessel is controlled.

* * * * *

UNITED STATES PATENT AND TRADEMARK OFFICE
CERTIFICATE OF CORRECTION

PATENT NO. : 6,569,672 B1  
DATED : May 27, 2003  
INVENTOR(S) : Edwin A. Rudd et al.

It is certified that error appears in the above-identified patent and that said Letters Patent is hereby corrected as shown below:

<u>Title page,</u>  
Item [75], Inventors, after the Inventor, "David J. Green", please delete "Winchester" and replace it with -- Fitzwilliam --

Signed and Sealed this

Twentieth Day of January, 2004

JON W. DUDAS  
*Acting Director of the United States Patent and Trademark Office*